US012565640B2

(12) United States Patent
Osafune et al.

(10) Patent No.: US 12,565,640 B2
(45) Date of Patent: Mar. 3, 2026

(54) METHOD FOR INDUCING URETERIC BUD-LIKE TISSUE

(71) Applicant: Kyoto University, Kyoto (JP)

(72) Inventors: Kenji Osafune, Kyoto (JP); Shinichi Mae, Kyoto (JP); Makoto Ryosaka, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 1631 days.

(21) Appl. No.: 16/763,875

(22) PCT Filed: Nov. 16, 2018

(86) PCT No.: PCT/JP2018/042567
§ 371 (c)(1),
(2) Date: Oct. 2, 2020

(87) PCT Pub. No.: WO2019/098349
PCT Pub. Date: May 23, 2019

(65) Prior Publication Data
US 2021/0009960 A1      Jan. 14, 2021

Related U.S. Application Data

(60) Provisional application No. 62/587,693, filed on Nov. 17, 2017.

(51) Int. Cl.
*C12N 5/071*          (2010.01)

(52) U.S. Cl.
CPC ...... *C12N 5/0686* (2013.01); *C12N 2501/119* (2013.01); *C12N 2501/155* (2013.01); *C12N 2501/16* (2013.01); *C12N 2501/999* (2013.01); *C12N 2506/02* (2013.01); *C12N 2506/45* (2013.01); *C12N 2513/00* (2013.01)

(58) Field of Classification Search
CPC ............ C12N 5/0686; C12N 2501/119; C12N 2501/155; C12N 2501/16; C12N 2501/999; C12N 2506/02; C12N 2506/45; C12N 2513/00; C12N 2501/113; C12N 2501/115; C12N 2501/13; C12N 2501/15; C12N 2501/385; C12N 2501/727; C12N 5/0687; A61K 35/22; A61K 35/12
See application file for complete search history.

(56) References Cited

U.S. PATENT DOCUMENTS

| | | |
|---|---|---|
| 2015/0284689 A1 | 10/2015 | Nigam |
| 2016/0143949 A1* | 5/2016 | Ingber .................... A61K 35/22 |
| | | 435/377 |
| 2018/0119095 A1 | 5/2018 | Osafune et al. |
| 2020/0010807 A1 | 1/2020 | Osafune et al. |

FOREIGN PATENT DOCUMENTS

| | | |
|---|---|---|
| EP | 3031905 A1 | 6/2016 |
| EP | 3147353 A1 | 3/2017 |
| EP | 3351626 A1 | 4/2018 |
| JP | 2018-183137 A | 11/2018 |
| WO | WO 2015/020113 A1 | 2/2015 |
| WO | WO 2015/178431 A1 | 11/2015 |
| WO | WO 2016/104717 A1 | 6/2016 |
| WO | WO 2017/047797 A1 | 3/2017 |
| WO | WO 2018/097127 A1 | 5/2018 |

OTHER PUBLICATIONS

Taguchi et al. (Higher-Order Kidney Organogenesis from Pluripotent Stem Cells, 2017, Cell Stem Cell 21, 730-746, Available online Nov. 9, 2017, Version of Record Dec. 7, 2017, Published: Nov. 9, 2017 (Year: 2017).*
Yuri, Shunsuke et al., (In Vitro Propagation and Branching Morphogenesis from Single Ureteric Bud Cells, Stem Cell Reports, Feb. 2017, vol. 8, pp. 401-416 (Year: 2017).*
Kitagaki et al., FGF8 is essential for formation of the ductal system in the male reproductive tract; Development 138, 5369-5378 (2011) doi:10.1242/dev.051888 (Year: 2011).*
V Kretzschmar, K. and Clevers, H., 2016. Organoids: modeling development and the stem cell niche in a dish. Developmental cell, 38 (6), pp. 590-600. (Year: 2016).*
Taguchi, A. and Nishinakamura, R., 2017. Higher-order kidney organogenesis from pluripotent stem cells. Cell stem cell, 21(6), pp. 730-746 and e1-e6 (Year: 2017).*
Ameku et al., "Identification of MMP1 as a novel risk fackor for intracranial aneurysims in ADPKD using iPSC models", Scientific Reports, 2016, vol. 6, 30013.
Araoka et al., "Efficient and Rapid Induction of Human iPSCs/ESCs into Nephrogenic Intermediate Mesoderm Using Small Molecule-Based Differentiation Methods", PLoS One, 2014, vol. 9, Issue 1, e84881.
Atsuta et al., "FGF8 coordinates tissue elongation and cell epithelialization during early kidney tubulogenesis", The Company of Biologists Ltd., Development, 2015, vol. 142, pp. 2329-2337.
Colvin et al., "Genomic Organization and Embryonic Expression of the Mouse Fibroblast Growth Factor 9 Gene", Developmental Dynamics, 1999, vol. 216, pp. 72-88.
Costantini et al., "Patterning a complex organ: branching morphogenesis and nephron segmentation in kidney development", Dev. Cell, 2010, vol. 18, No. 5, pp. 698-712.
Faure et al., "Endogenous Patterns of BMP Signaling during Early Chick Development", Developmental Biology, 2002, vol. 244, pp. 44-65.

(Continued)

*Primary Examiner* — Fereydoun G Sajjadi
*Assistant Examiner* — Masudur Rahman
(74) *Attorney, Agent, or Firm* — Lathrop GPM LLP; James H. Velema, Esq.; Judith Stone-Hulslander

(57)          ABSTRACT

An object of the present application is to provide a method for inducing the differentiation from pluripotent stem cells, particularly iPS cells and ES cells, into ureteric bud cells. Another object of the present application is to provide a system for producing ureteric bud-like tissue from pluripotent stem cells through each stage of differentiations, i.e. anterior primitive streak cells, anterior intermediate mesoderm cells and Wolffian duct cells. Yet another object of the present application is to provide a method for maintaining ureteric bud-like organoids. Another object of the present application is to provide a method for expansion-culturing ureteric bud-like tip tissue.

20 Claims, 25 Drawing Sheets

(56) References Cited

OTHER PUBLICATIONS

International Preliminary Report on Patentability for PCT International Patent Application No. PCT/JP2018/042567, mailed May 19, 2020, 6 pages.

International Search Report for PCT International Patent Application No. PCT/JP2018/042567, mailed Feb. 5, 2019, 2 pages.

Kobayashi et al., "Six2 defines and regulates a multipotent self-renewing nephron progenitor population throughout mammalian kidney development", Cell Stem Cell, 2008, vol. 3, No. 2, pp. 169-181.

Loh et al., "Mapping the pairwise choices leading from pluripotency to human bone, heart and other mesoderm cell-types", Cell, 2016, vol. 166, No. 2, pp. 451-467.

Mae et al., "Generation of Branching ureteric bud tissues from human pluripotent stem cells", Biochemical and Biophysical Research Communications, 2018, vol. 495, pp. 954-961.

Mae et al., "Monitoring and robust induction of nephrogenic intermediate mesoderm from human pluripotent stem cells", Nat. Commun., 2013, vol. 4, 1367.

Morizane et al., "Nephron organoids derived from human pluripotent stem cells model kidney development and injury", Nat. Biotechnol., 2015, vol. 33, No. 11, pp. 1193-1200.

Obara-Ishihara et al., "The surface ectoderm is essential for nephric duct formation in intermediate mesoderm", Development 126, 1999, pp. 1103-1108.

Oceguera-Yanez et al., "Engineering the AAVS1 locus for consistent and scalable transgene expression in human iPSCs and their differentiated derivatives", Methods, 2016, vol. 101, pp. 43-55.

Oku et al., "Small molecules inhibiting the nuclear localization of YAP/TAZ for chemotherapeutics and chemosensitizers against breast cancer", FEBS Open Bio 5, 2015, pp. 542-549.

Osafune et al., "Identification of multipotent progenitors in the embryonic mouse kidney by a novel colony-forming assay", Development, 2006, vol. 133, pp. 151-161.

Oxburgh et al., "Bone morphogenetic protein signaling in nephron progenitor cells", Pediatr. Nephrol., 2014, vol. 29, No. 4, pp. 531-536.

Reginensi et al., "A critical role for NF2 and the Hippo pathway in branching morphogenesis", Nature Communications, 2016, vol. 7, 12309.

So et al., "Cloning and expression analysis of a mouse gene related to *Drosophila* odd-skipped", Mechanisms of Development, 1999, vol. 84, pp. 157-160.

Suemori et al., "Efficient establishment of human embryonic stem cell lines and long-term maintenance with stable karyotype by enzymatic bulk passage", Biochemical and Biophysical Research Communications, 2006, vol. 345, pp. 926-932.

Taguchi et al., "Higher-Order Kidney Organogenesis from Pluripotent Stem Cells", Cell Stem Cell, 2017, vol. 21, pp. 730-746.

Taguchi et al., "Redefining the In Vivo Origin Metanephric Nephron Progenitors Enables Generation of Complex Kidney Structures from Pluripotent Stem Cells", Cell Stem Cell, 2014, vol. 14, pp. 53-67.

Takasato et al., "Kidney organoids from human iPS cells contain multiple lineages and model human nephrogenesis", Nature, 2015, vol. 526, pp. 564-568.

Wang et al., "Odd-skipped related 1 (Odd1) is an essential regulator of heart and urogenital development", Developmental Biology, 2005, vol. 288, pp. 582-594.

Wilm et al., "The forkhead genes, Foxc1 and Foxc2, regulate paraxial versus intermediate mesoderm cell fate", Developmental Biology, 2004, vol. 271, pp. 176-189.

山下和成, 西中村隆一, 腎臓の発生 その分子機構, 蛋白質核酸酵素, 2005, vol. 50, no. 6, pp. 644-649, non-official translation (Yamashita et al., "Development of kidney and its molecular mechanism", Protein, nucleic acid and enzyme, 2005, vol. 50, No. 6, pp. 644-649.).

Yoshino et al., "Hedgehog-BMP signalling establishes dorsoventral patterning in lateral plate mesoderm to trigger gonadogenesis in chicken embryos", Nature Communications, 2016, vol. 7, 12561.

Yuri et al., "In Vitro Propagation and Branching Morphogenesis from Single Ureteric Bud Cells", Stem Cell Reports, 2017, 8 (2017) 401-416.

Yuri, Shunsuke et al., "In Vitro Propagation and Branching Morphogenesis from Single Ureteric Bud Cells", Stem Cell Reports, Feb. 14, 2017, vol. 8, pp. 401-416.

* cited by examiner

Figure 1E
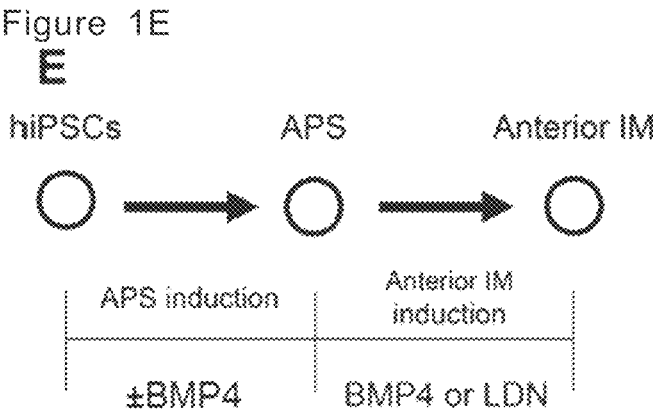
Figure 1F
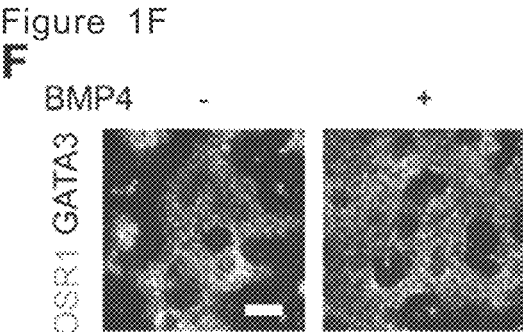
Figure 1G

H

| BMP4 to APS induction | - | + | + |
| LDN to anterior IM induction | - | - | + |

Figure 2E
E
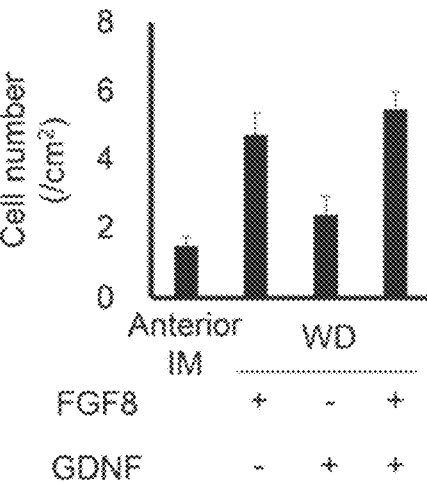
Figure 2F
F
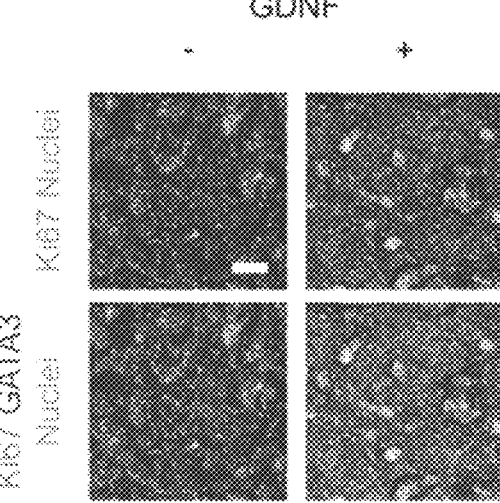
Figure 2G
G

Figure 2H
H
E-CADHERIN   PAX2 GATA3   LHX1 PAX2   CK8 PAX2
GATA3 Nuclei    Nuclei       Nuclei       Nuclei
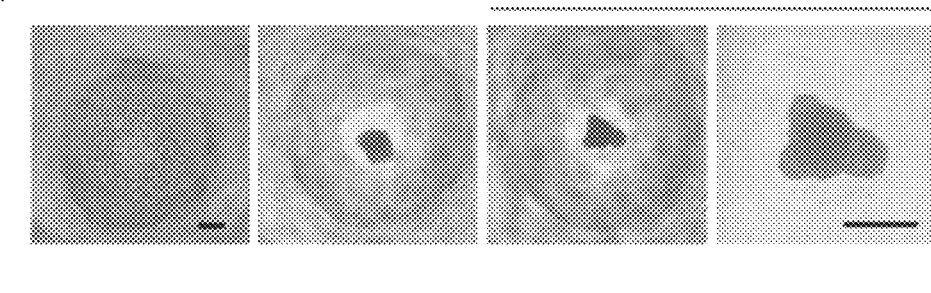
Figure 3A
A       0 day          1 day                    2 days
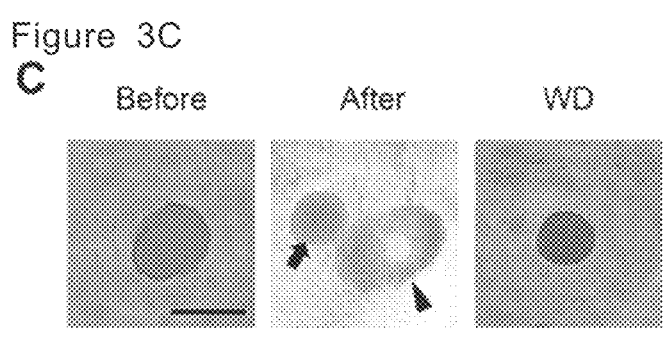
Figure 3B
B
E-CADHERIN
GATA3 Nuclei
Figure 3C
C       Before        After        WD Figure 3D
D
| E-CADHERIN<br>GATA3 | E-CADHERIN<br>PAX2 | RET<br>GATA3 |
|---|---|---|
| CALB1<br>PAX2 | PAX2<br>CDH16 | SOX9<br>PAX2 |
|---|---|---|
Figure 3E
E
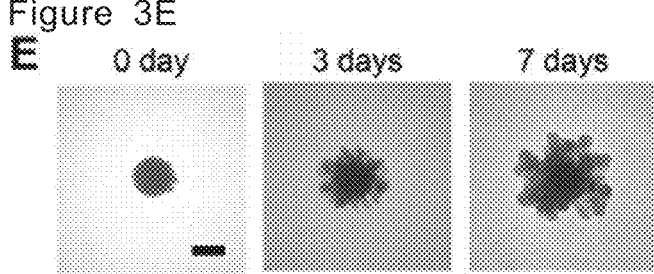
0 day     3 days     7 days
Figure 3F
F
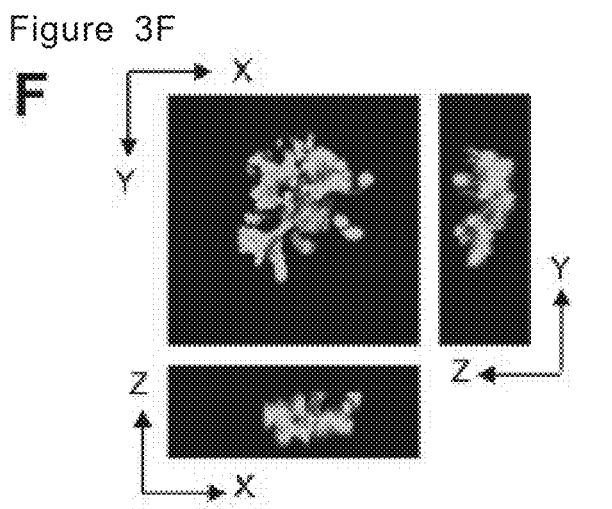

Figure 4

| Pre-differentiation | APS | Anterior IM | | WD elongation | WD maturation | UB budding and branching |
|---|---|---|---|---|---|---|
| AK02N | Essential 6 | | | | | |
| iMatrix silk (2D) | | | Matrigel (2D) | | Low attachment plate | Matrigel (3D) |
| Y | A<br>C3<br>B | F8<br>TT<br>A83<br>LDN | F8<br>TT<br>A83<br>LDN<br>Y | C1<br>LDN<br>F8<br>G | G<br>F1<br>TT<br>C3<br>Tzv | G<br>F1<br>TT<br>C3<br>Tzv |
| 1 d | 1 d | 2 d | 1 d | 2 d | 2 d | 15 d |

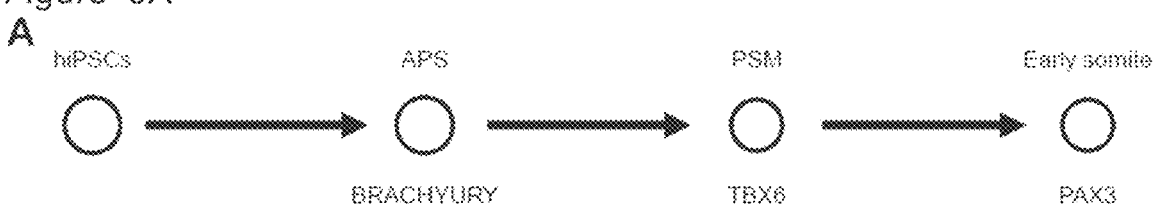

hiPSCs → APS → PSM → Early somite

BRACHYURY    TBX6    PAX3

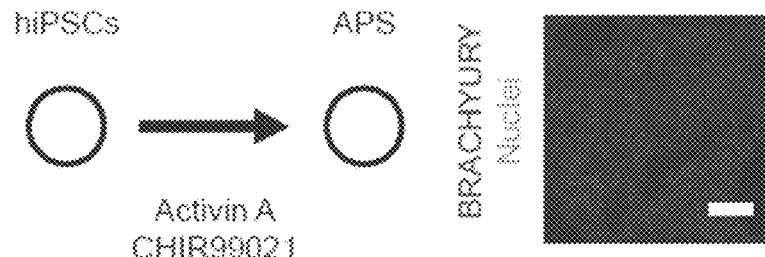

hiPSCs → APS

Activin A
CHIR99021

BRACHYURY / Nuclei

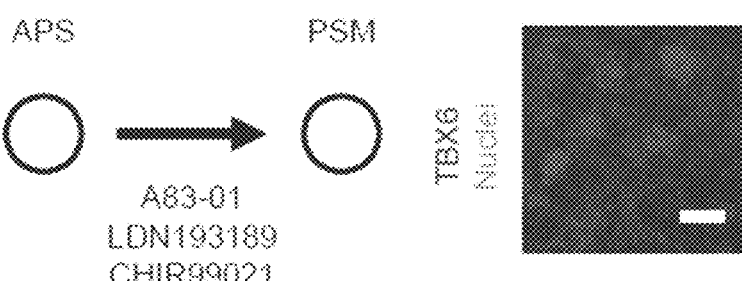

APS → PSM

A83-01
LDN193189
CHIR99021

TBX6 / Nuclei

Figure 5D
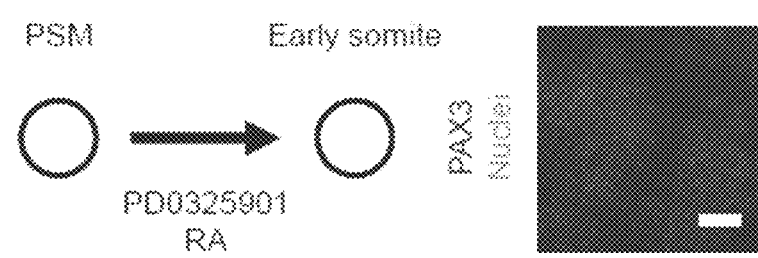
Figure 5E
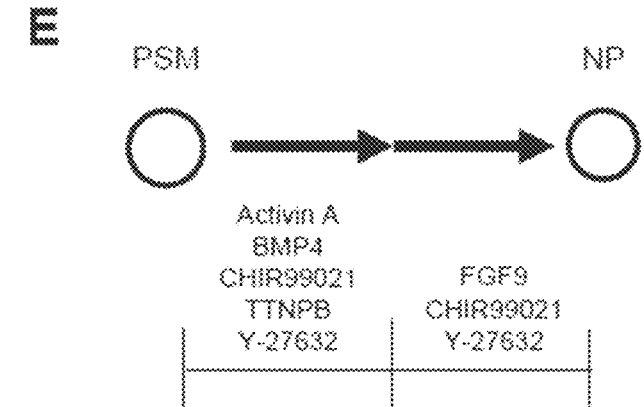
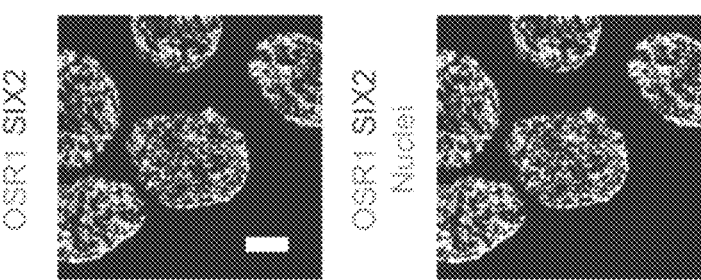
Figure 5F
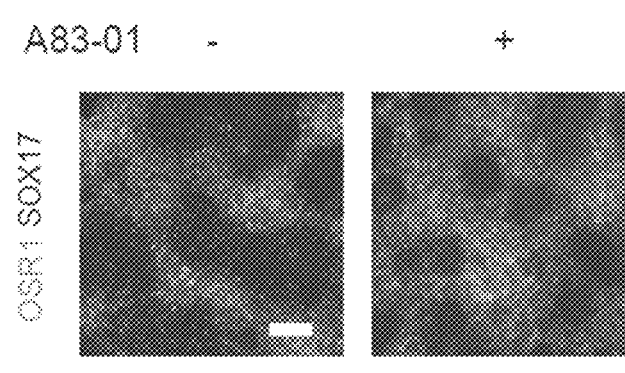

A

B

| Pre-differentiation | Anterior PS | Anterior IM | | ND elongation |
|---|---|---|---|---|
| 10 μM Y27632 | 100 ng/ml Activin A<br>3 μM CHIR99021 | 200 ng/ml FGF8<br>0.1 μM TTNPB<br>1 μM A83-01<br>0.1 μM LDN193189 | 200 ng/ml FGF8<br>0.1 μM TTNPB<br>1 μM A83-01<br>0.1 μM LDN193189<br>10 μM Y27632 | 1 μM CHIR99021<br>0.1 μM LDN193189<br>200 ng/ml FGF8<br>0.1 μM TTNPB<br>100 ng/ml GDNF |

| 1 d | 1 d | 2 d | 1 d | 2 d |

| Pre-differentiation | Anterior PS | Anterior IM | | ND elongation | ND maturation |
|---|---|---|---|---|---|
| 10 µM Y27632 | 100 ng/ml Activin A<br>3 µM CHIR99021 | 200 ng/ml FGF8<br>0.1 µM TTNPB<br>1 µM A83-01<br>0.1 µM LDN193189 | 200 ng/ml FGF8<br>0.1 µM TTNPB<br>1 µM A83-01<br>0.1 µM LDN193189<br>10 µM Y27632 | 1 µM CHIR99021<br>0.1 µM LDN193189<br>200 ng/ml FGF8<br>0.1 µM TTNPB<br>100 ng/ml GDNF | 1 µM CHIR99021<br>0.1 µM LDN193189<br>200 ng/ml FGF8<br>0.1 µM TTNPB<br>100 ng/ml GDNF |

| 1 d | 1 d | 2 d | 1 d | 2 d | X d |

Figure 9C

|  | Before | After |
|---|---|---|

E-CADHERIN GATA3 Nuclei

E-CADHERIN PAX2 Nuclei

Figure 10A

| Pre-differentiation | Anterior PS | Anterior IM | | NE elongation | NE maturation | UB budding |
|---|---|---|---|---|---|---|
| 10 μM Y27632 | 100 ng/ml Activin A<br>3 μM CHIR99021 | 200 ng/ml FGF8<br>0.1 μM TTNPB<br>1 μM A83-01<br>0.1 μM LDN193189 | 200 ng/ml FGF8<br>0.1 μM TTNPB<br>1 μM A83-01<br>0.1 μM LDN193189<br>10 μM Y27632 | 1 μM CHIR99021<br>0.1 μM LDN193189<br>200 ng/ml FGF8<br>0.1 μM TTNPB<br>100 ng/ml GDNF | 1 μM CHIR99021<br>0.1 μM LDN193189<br>200 ng/ml FGF8<br>0.1 μM TTNPB<br>100 ng/ml GDNF<br>10 μM Y27632 | 1 μM CHIR99021<br>0.1 μM LDN193189<br>200 ng/ml FGF8<br>0.1 μM TTNPB<br>100 ng/ml GDNF<br>3 % Matrigel |
| 1 d | 1 d | 2 d | 1 d | 2 d | 2 d | 6 d |

Figure 10B

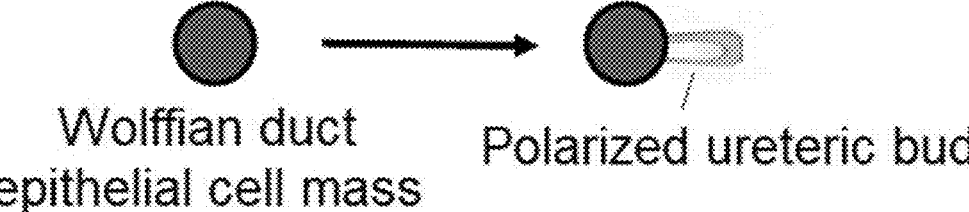

Wolffian duct
epithelial cell mass → Polarized ureteric bud

Figure 10C

| 0 d | 2 d | 4 d |
|---|---|---|

Figure 10D

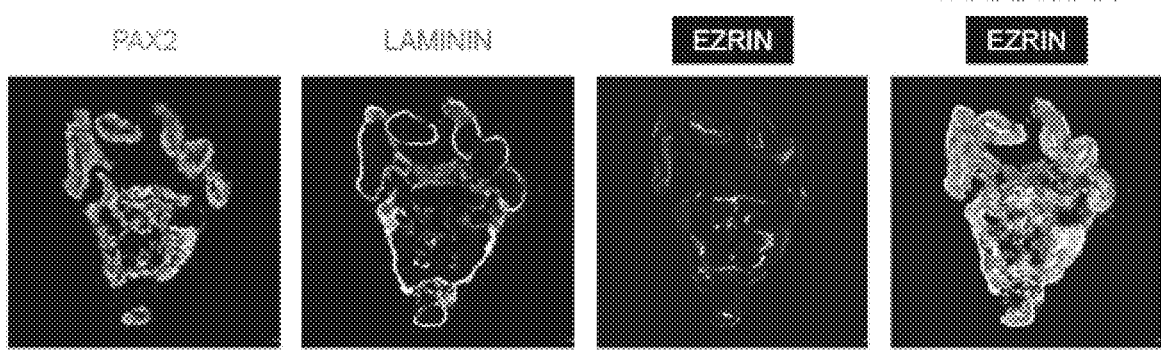

Figure 11A

| Pre-differentiation | Anterior PS | Anterior IM | | ND elongation | ND maturation |
|---|---|---|---|---|---|
| 10 μM Y27632 | 100 ng/ml Activin A<br>3 μM CHIR99021 | 200 ng/ml FGF8<br>0.1 μM TTNPB<br>1 μM A83-01<br>0.1 μM LDN193189 | 200 ng/ml FGF8<br>0.1 μM TTNPB<br>1 μM A83-01<br>0.1 μM LDN193189<br>10 μM Y27632 | 1 μM CHIR99021<br>0.1 μM LDN193189<br>200 ng/ml FGF8<br>0.1 μM TTNPB<br>100 ng/ml GDNF | 1 μM CHIR99021<br>0.1 μM LDN193189<br>200 ng/ml FGF8<br>0.1 μM TTNPB<br>100 ng/ml GDNF<br>10 μM Y27632 |
| 1 d | 1 d | 2 d | 1 d | 2 d | 2 d |

Cryopreservable

Figure 11B

E-CADHERIN E-CADHERIN
PAX2 Nuclei GATA3 Nuclei

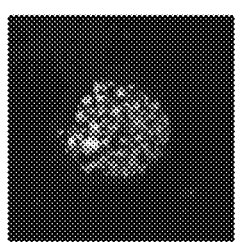 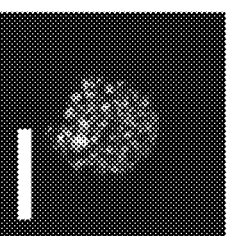

Figure 12A

| Pre-differentiation | Anterior PS | Anterior IM | ND elongation | ND maturation | UB budding | UB branching |
|---|---|---|---|---|---|---|
| 10 μM Y27632 | 100 ng/ml Activin A<br>3 μM CHIR99021 | 200 ng/ml FGF9<br>0.1 μM TTNPB<br>1 μM A83-01<br>0.1 μM LDN193189<br>10 μM Y27632 | 1 μM CHIR99021<br>0.1 μM LDN193189<br>200 ng/ml FGF9<br>0.1 μM TTNPB<br>100 ng/ml GDNF | 1 μM CHIR99021<br>0.1 μM LDN193189<br>200 ng/ml FGF9<br>0.1 μM TTNPB<br>100 ng/ml GDNF<br>10 μM Y27632 | 1 μM CHIR99021<br>0.1 μM LDN193189<br>200 ng/ml FGF9<br>0.1 μM TTNPB<br>100 ng/ml GDNF<br>2 % Matrigel | 1 μM CHIR99021<br>0.1 μM LDN193189<br>200 ng/ml FGF9<br>0.1 μM TTNPB<br>100 ng/ml GDNF<br>2 % Matrigel |

1 d | 1 d | 2 d | 1 d | 2 d | 2 d | 6 d | 14 d

Mechanical isolation of UB

Figure 12B
Isolation
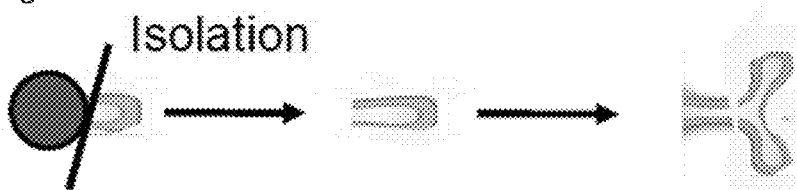
Figure 12C
0 d        3 d        7 d        10 d
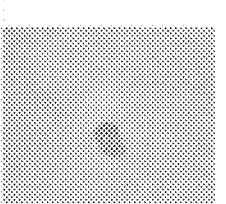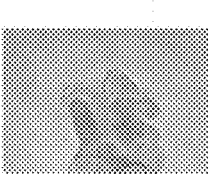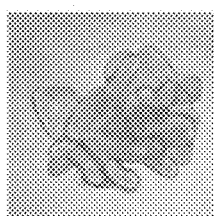
Figure 12D
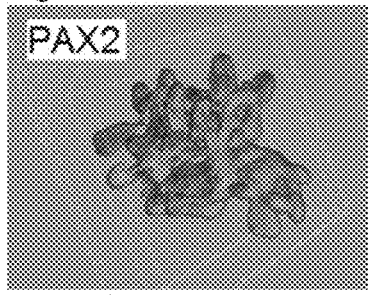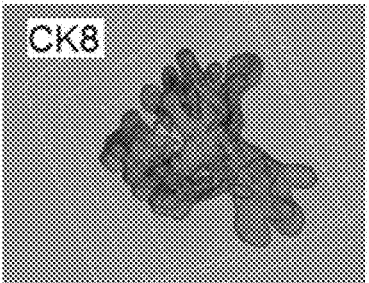
Figure 12E
PAX2 RET CK8
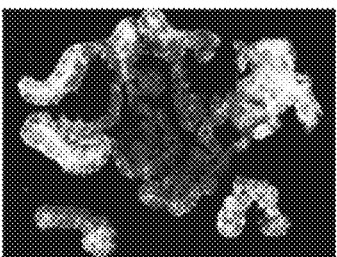
Figure 12F
PAX2      EZRIN      LAMININ      PAX2 EZRIN LAMININ
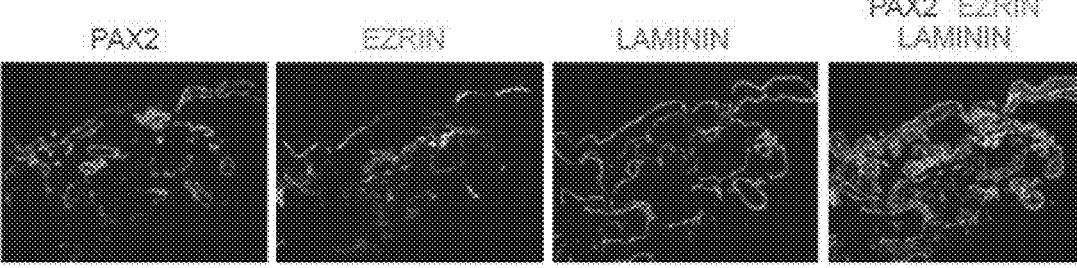

Figure 13A

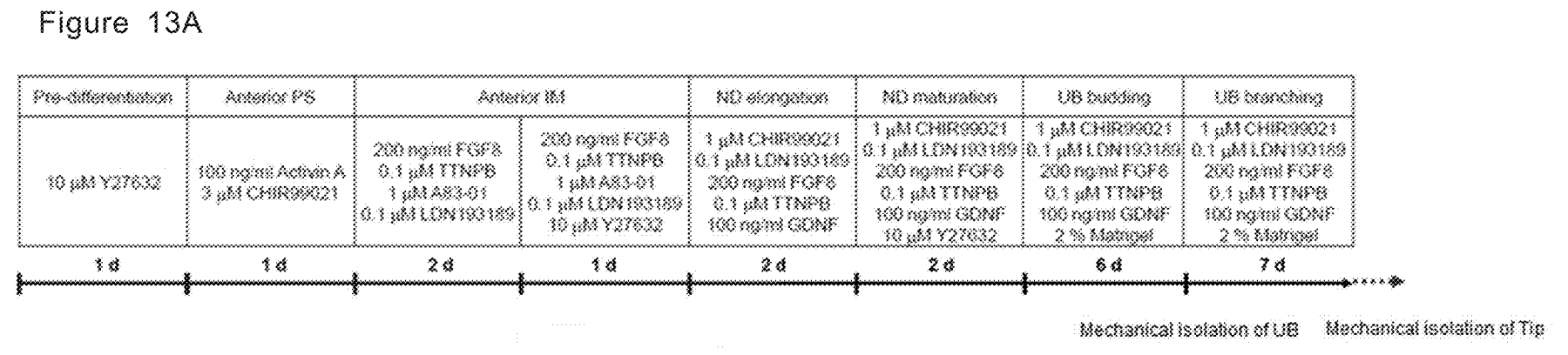

| Pre-differentiation | Anterior PS | Anterior IM | Anterior IM | MD elongation | MD maturation | UB budding | UB branching |
|---|---|---|---|---|---|---|---|
| 10 µM Y27632 | 100 ng/ml Activin A<br>3 µM CHIR99021 | 200 ng/ml FGF9<br>0.1 µM TTNPB<br>1 µM A83-01<br>0.1 µM LDN193189 | 200 ng/ml FGF9<br>0.1 µM TTNPB<br>1 µM A83-01<br>0.1 µM LDN193189<br>10 µM Y27632 | 1 µM CHIR99021<br>0.1 µM LDN193189<br>200 ng/ml FGF9<br>0.1 µM TTNPB<br>100 ng/ml GDNF | 1 µM CHIR99021<br>0.1 µM LDN193189<br>200 ng/ml FGF9<br>0.1 µM TTNPB<br>100 ng/ml GDNF<br>10 µM Y27632 | 1 µM CHIR99021<br>0.1 µM LDN193189<br>200 ng/ml FGF9<br>0.1 µM TTNPB<br>100 ng/ml GDNF<br>2% Matrigel | 1 µM CHIR99021<br>0.1 µM LDN193189<br>200 ng/ml FGF9<br>0.1 µM TTNPB<br>100 ng/ml GDNF<br>2% Matrigel |
| 1 d | 2 d | 1 d | 1 d | 2 d | 2 d | 6 d | 7 d |

Mechanical isolation of UB    Mechanical isolation of Tip

Figure 14A

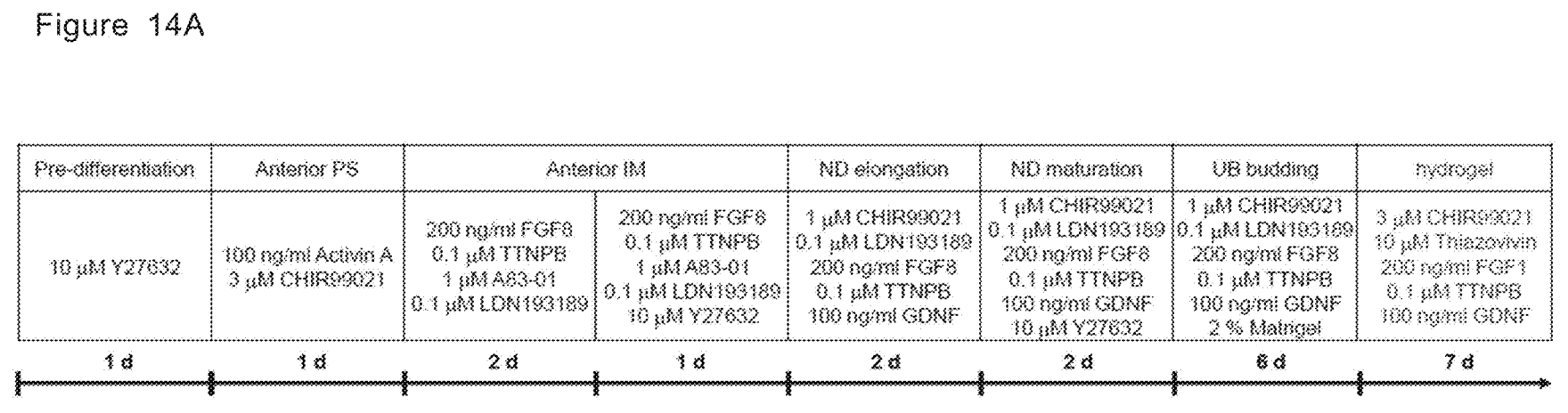

| Pre-differentiation | Anterior PS | Anterior IM | | ND elongation | ND maturation | UB budding | hydrogel |
|---|---|---|---|---|---|---|---|
| 10 µM Y27632 | 100 ng/ml Activin A<br>3 µM CHIR99021 | 200 ng/ml FGF8<br>0.1 µM TTNPB<br>1 µM A83-01<br>0.1 µM LDN193189 | 200 ng/ml FGF8<br>0.1 µM TTNPB<br>1 µM A83-01<br>0.1 µM LDN193189<br>10 µM Y27632 | 1 µM CHIR99021<br>0.1 µM LDN193189<br>200 ng/ml FGF8<br>0.1 µM TTNPB<br>100 ng/ml GDNF | 1 µM CHIR99021<br>0.1 µM LDN193189<br>200 ng/ml FGF8<br>0.1 µM TTNPB<br>100 ng/ml GDNF<br>10 µM Y27632 | 1 µM CHIR99021<br>0.1 µM LDN193189<br>200 ng/ml FGF8<br>0.1 µM TTNPB<br>100 ng/ml GDNF<br>2 % Matrigel | 3 µM CHIR99021<br>10 µM Thiazovivin<br>200 ng/ml FGF1<br>0.1 µM TTNPB<br>100 ng/ml GDNF |
| 1 d | 1 d | 2 d | 1 d | 2 d | 2 d | 6 d | 7 d |

Day 7

Figure 15A

| Pre-differentiation | Anterior PS | Anterior IM | | ND elongation | ND maturation | UB budding | hydrogel | UB branching |
|---|---|---|---|---|---|---|---|---|
| 10 μM Y27632 | 100 ng/ml Activin A<br>3 μM CHIR99021 | 200 ng/ml FGF8<br>0.1 μM TTNPB<br>1 μM A83-01<br>0.1 μM LDN193189 | 200 ng/ml FGF9<br>0.1 μM TTNPB<br>1 μM A83-01<br>0.1 μM LDN193189<br>10 μM Y27632 | 1 μM CHIR99021<br>0.1 μM LDN193189<br>200 ng/ml FGF8<br>0.1 μM TTNPB<br>100 ng/ml GDNF | 1 μM CHIR99021<br>0.1 μM LDN193189<br>200 ng/ml FGF9<br>0.1 μM TTNPB<br>100 ng/ml GDNF<br>10 μM Y27632 | 1 μM CHIR99021<br>0.1 μM LDN193189<br>200 ng/ml FGF9<br>0.1 μM TTNPB<br>100 ng/ml GDNF<br>2 % Matrigel | 3 μM CHIR99021<br>10 μM Thiazovivin<br>200 ng/ml FGF1<br>0.1 μM TTNPB<br>100 ng/ml GDNF | 1 μM CHIR99021<br>0.1 μM LDN193189<br>200 ng/ml FGF8<br>0.1 μM TTNPB<br>100 ng/ml GDNF<br>2 % Matrigel |
| 1 d | 1 d | 2 d | 1 d | 2 d | 2 d | 6 d | 6 d | 14 d | hydrogel

E6 +5F
2 % matrigel

| EZRIN | LAMININ | CK8 | GATA3 |

| Suspension culture (non-adhesive plate) | 3-dimensional culture (hydrogel) | Adherent culture (Matrix-silk) |
|---|---|---|
| 1 µM CHIR99021 0.1 µM LDN193189 200 ng/ml FGF9 100 ng/ml GDNF 0.1 µM TTNPB 2% Matrigel | 100 ng/ml GDNF 200 ng/ml FGF1 3 µM CHIR99021 0.1 µM TTNPB 10 µM Thiazovivin | 1 µM IWR-1 1 µM A83-01 |

| 6 d | 7 d | 7 d |

Nephric duct        UB budding        UB tip        Collecting duct progenitor cell

METHOD FOR INDUCING URETERIC BUD-LIKE TISSUE

RELATED APPLICATIONS

This application is a 35 U.S.C. § 371 filing of International Patent Application No. PCT/JP2018/042567, filed Nov. 16, 2018, which claims priority U.S. Provisional Patent Application Ser. No. 62/587,693, filed Nov. 17, 2017, the entire disclosures of which are hereby incorporated herein by reference.

TECHNICAL FIELD

The present application relates to a method for inducing ureteric bud-like tissue. Specifically, the present application relates to a method for inducing ureteric bud-like tissue from pluripotent stem cells, in particular human pluripotent stem cells.

BACKGROUND ART

At present, the number of chronic kidney disease (CKD) patients in Japan is estimated to be about 13 million, and CKD is called a new national disease. There are few curative treatments for chronic kidney disease and there are more than 320,000 end-stage chronic renal failure patients who require dialysis therapy due to progression of the disease, which is a serious problem for medical science and medical economics. Kidney transplantation is one of the curative treatments for chronic kidney disease including end-stage chronic renal failure, but its demand far exceeds its supply due to severe shortage of donor organs.

In order to solve the shortage of donor organs for kidney transplantation and to develop novel cell therapies for chronic kidney disease, it is necessary to establish a method for efficiently producing kidney cells and kidney tissues from iPS cells.

The kidney is derived from intermediate mesoderm, which is an early embryonic tissue. For vertebrates, the intermediate mesoderm forms three kidneys: pronephros, mesonephros and metanephros. For mammals, metanephros forms adult kidney. The metanephros is formed by the interaction between two tissues, mesenchyme, which differentiates into nephron and interstitium of the adult kidney, and ureteric bud, which differentiates into the collecting duct and parts of the lower renal pelvis, ureter and bladder of the adult kidney (non-patent literature 1 and 2). In addition, it has been recently reported that the intermediate mesoderm is divided into two sites, anterior and posterior, and ureteric bud emerges from the anterior intermediate mesoderm and mesenchyme emerges from the posterior intermediate mesoderm (non-patent literature 3).

If a method for efficiently inducing the differentiation from human iPS cells or human ES cells into ureteric bud cells/tissues can be established, the cells/tissues can be used for solving the shortage of donors for kidney transplantation by three-dimensionally remodeling the kidney and used as a source of collecting duct cells or lower urinary tract cells for a cell therapy in the future. In addition, it can be expected to develop the research on the drug evaluation system for nephrotoxicity using collecting duct cells, lower urinary tract cells, and kidney tissues containing them, and the production of disease model and therapeutic drug development using kidney cells and tissues produced from disease-specific iPS cells.

The ureteric bud first emerges as a protrusion from the caudal end of the Wolffian duct cell and then repeats branching to differentiate into renal collecting ducts and urinary tract epithelia. Producing the ureteric bud tissue forming branching structure can be useful for elucidating the mechanism of kidney development and kidney disease.

The inventors have established a method for inducing the differentiations from pluripotent stem cells into various types of cells including pancreatic hormone-producing cells, pancreatic blast cells, biliary epithelial progenitor cells, and hepatocytes (patent literatures 1 to 5). A method for selectively inducing the differentiation from human iPS cells or human ES cells into ureteric bud cells has not been known so far.

CITATION LIST

Patent Literature

[Patent Literature 1] WO2015/020113
[Patent Literature 2] WO2015/178431
[Patent Literature 3] WO2017/047797
[Patent Literature 4] WO2018/097127
[Patent Literature 5] WO2016/104717

Non-Patent Literature

[Non-Patent Literature 1] Osafune K., et al., Development 2006; 133: 151-61.
[Non-Patent Literature 2] Kobayashi A., et al., Cell Stem Cell 2008; 3: 169-81.
[Non-Patent Literature 3] Taguchi A., et al., Cell Stem Cell. 2014; 14: 53-67.

SUMMARY OF INVENTION

Technical Problem

An object of the present application is to provide a method for inducing the differentiation from pluripotent stem cells, particularly iPS cells or ES cells, into ureteric bud cells. Another object of the present application is to provide a system for producing ureteric bud-like tissues from pluripotent stem cells through each stage of differentiations, i.e. anterior primitive streak cells, anterior intermediate mesoderm cells and Wolffian duct cells. Yet another object of the present application is to provide a method for maintaining ureteric bud-like organoids. Another object of the present application is to provide a method for expansion-culturing ureteric bud-like organoids. Yet another object of the present application is to provide a method for inducing the differentiation from pluripotent stem cells into collecting duct progenitor cells.

Solution to Problem

The present application provides a method for inducing an early Wolffian duct cell, comprising the following steps:

(1) culturing an anterior primitive streak cell in the presence of a fibroblast growth factor, a retinoic acid receptor agonist, a TGFβ inhibitor and a BMP inhibitor under a two-dimensional culture condition to obtain an anterior intermediate mesoderm cell culture, and (2) culturing the anterior intermediate mesoderm cell culture in the presence of a GSK3β inhibitor, a BMP inhibitor, a fibroblast growth factor and a glial cell line-derived neurotrophic factor under a two-dimensional culture condition. In step (2), the medium may further comprise a retinoic acid receptor agonist.

In this aspect, the method may further comprise the step of culturing a pluripotent stem cell in the presence of an activator of activin receptor kinase 4,7, a GSK3β inhibitor and BMP4 under a two-dimensional culture condition to obtain the anterior primitive streak cell. Alternatively, the anterior primitive streak cell may be obtained by another known method. Accordingly, this aspect provides a method for inducing an early Wolffian duct cell from a pluripotent stem cell.

The present application also provides a method for cryo-preserving an induced early Wolffian duct cell. The early Wolffian duct cell cryopreserved and thawed by the method of the present application can be used as an early Wolffian duct cell in the following aspect.

The present application also provides a method for inducing ureteric bud-like tissue, comprising the following steps:

(3) culturing an early Wolffian duct cell in the presence of a glial cell line-derived neurotrophic factor, a fibroblast growth factor, a retinoic acid receptor agonist, a GSK3β inhibitor and a Yes-associated protein (YAP) activity inhibitor under a suspension culture condition to obtain a mature Wolffian duct cell aggregate, and (4) culturing the mature Wolffian duct cell aggregate in the presence of a glial cell line-derived neurotrophic factor, a fibroblast growth factor, a retinoic acid receptor agonist, a GSK3β inhibitor and a Yes-associated protein (YAP) activity inhibitor under a three-dimensional culture condition. In this aspect, the early Wolffian duct cell may be the cell induced by the method of the present application, or the cell cryopreserved and then thawed by the method of the present application. Accordingly, this aspect provides a method for inducing ureteric bud-like tissue from a pluripotent stem cell.

In another aspect, the present application provides a method for inducing ureteric bud-like tissue, comprising the following steps:

(3') culturing an early Wolffian duct cell in the presence of a GSK3β inhibitor, a BMP inhibitor, a fibroblast growth factor, a retinoic acid receptor agonist and a glial cell line-derived neurotrophic factor under a suspension culture condition to obtain a mature Wolffian duct cell aggregate, and (4') culturing the mature Wolffian duct cell aggregate in the presence of a GSK3β inhibitor, a BMP inhibitor, a fibroblast growth factor, a retinoic acid receptor agonist and a glial cell line-derived neurotrophic factor under a suspension culture condition. In this aspect, the early Wolffian duct cell may be the cell induced by the method of the present application, or the cell cryopreserved and then thawed by the method of the present application.

The present application also provides a method for inducing a ureteric bud-like organoid, comprising the following steps:

obtaining a ureteric bud-like tissue culture by the method of the present application, (5-1) isolating ureteric bud-like tissue, and (5-2) culturing the isolated ureteric bud-like tissue in the presence of a GSK3β inhibitor, a BMP inhibitor, a fibroblast growth factor, a retinoic acid receptor agonist and a glial cell line-derived neurotrophic factor under a suspension culture condition.

The present application also provides a method for maintaining a ureteric bud-like organoid, comprising the following steps:

obtaining a ureteric bud-like organoid culture by the method of the present application, (6-1) truncating the tip region of the ureteric bud-like organoid to obtain ureteric bud-like tip tissue, (6-2) culturing the ureteric bud-like tip tissue in the presence of a GSK3β inhibitor, a BMP inhibitor, a fibroblast growth factor, a retinoic acid receptor agonist and a glial cell line-derived neurotrophic factor under a suspension culture condition to induce a ureteric bud-like organoid, and (6-3) repeating steps (6-1) and (6-2).

The present application also provides a method for expansion-culturing ureteric bud-like tip tissue, comprising the following steps:

obtaining a ureteric bud-like tissue culture by the method of the present application, (5'-1) dissociating tissue in the ureteric bud-like tissue culture into single cells, and (5'-2) culturing the single cells in the presence of a glial cell line-derived neurotrophic factor, a fibroblast growth factor, a retinoic acid receptor agonist, a GSK3β inhibitor and a Yes-associated protein (YAP) activity inhibitor under a three-dimensional culture condition.

The present application also provides a method for inducing a ureteric bud-like organoid, comprising the following steps:

obtaining ureteric bud-like tip tissue by the method of the present application, and (6') culturing the ureteric bud-like tip tissue in the presence of a GSK3β inhibitor, a BMP inhibitor, a fibroblast growth factor, a retinoic acid receptor agonist and a glial cell line-derived neurotrophic factor under a suspension culture condition.

The present application also provides a method for inducing a collecting duct progenitor cell, comprising the following steps:

obtaining ureteric bud-like tip tissue by the method of the present application, (6"-1) dissociating the ureteric bud-like tip tissue into single cells, and (6"-2) culturing the single cells in the presence of a Wnt signal inhibitor and a TGFβ signal inhibitor under an adherent culture condition. Accordingly, this aspect provides a method for inducing a collecting duct progenitor cell from a pluripotent stem cell.

Effects of the Invention

The present application provides the methods described in the claims Ureteric bud-like tissue can be relatively simply and efficiently produced by the methods of the present application.

5

6

Figure 1A:
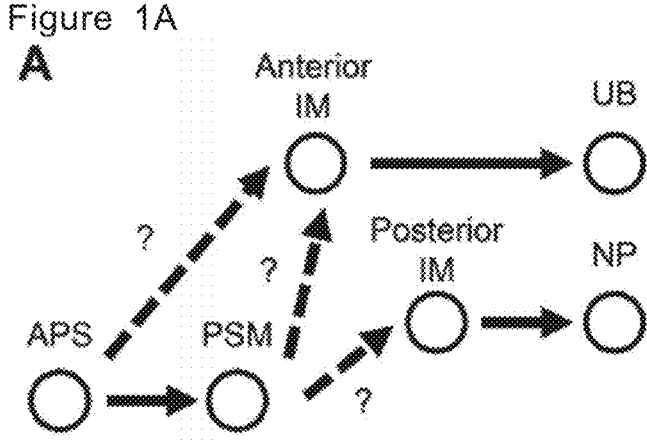
FIG. 1A Schematic of the differentiation from anterior primitive streak (APS) cells into ureteric bud (UB) and nephron progenitor (NP) cells.
Figure 1B:
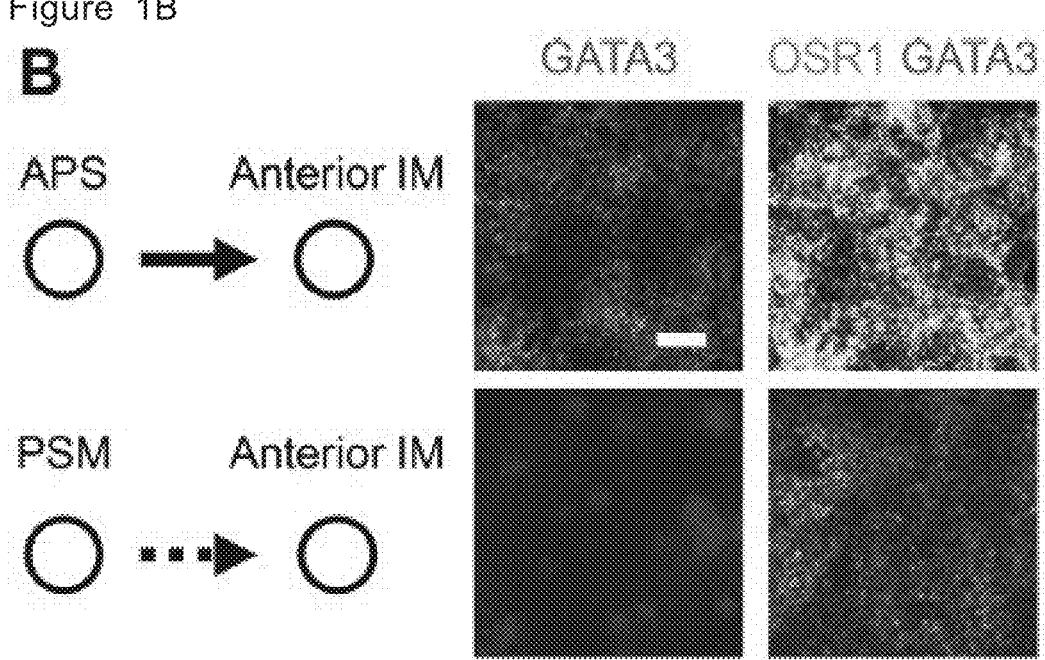
FIG. 1B Immunostaining analysis for OSR1 (GFP, green) and GATA3 (red). Treatment with FGF8 and TTNPB induces anterior primitive streak (APS) cells, but not pre-somitic mesoderm (PSM) cells, into anterior intermediate mesoderm (Anterior IM)-like cells. Scale bars, 100 μm.
Figures 1C, 1D:
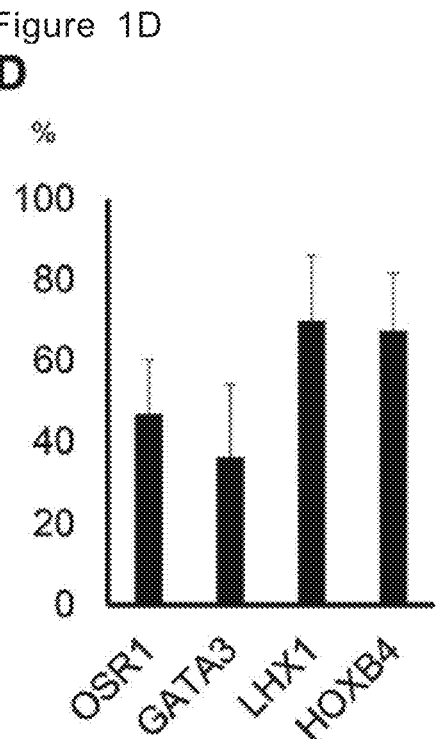
FIG. 1C Immunostaining analysis for anterior intermediate mesoderm markers. Scale bars, 100 μm.

FIG. 1D Quantification of the differentiation into cells expressing anterior intermediate mesoderm markers, OSR1, GATA3, LHX1 and HOXB4, by flow cytometry analysis. The data from four independent experiments are presented as the mean±s.d. (n=4).

FIG. 1E The effects of adding BMP4 and LDN193189 to the induction stages of anterior primitive streak (APS) and anterior intermediate mesoderm (Anterior IM) on the differentiation of OSR1$^+$GATA3$^+$ cells. hiPSCs were treated with 100 ng/ml Activin A and 3 µM CHIR99021 with or without 10 ng/ml BMP4, and anterior primitive streak cells were treated with 0.1 µM TTNPB, 1 µM A83-01 and 200 ng/ml FGF8 with 10 ng/ml BMP4 or 0.1 µM LDN193189.

FIG. 1F The effects of adding BMP4 and LDN193189 to the induction stages of anterior primitive streak (APS) and anterior intermediate mesoderm (Anterior IM) on the differentiation of OSR1$^+$GATA3$^+$ cells. Immunostaining analysis for OSR1 (GFP, green) and GATA3 (red). Adding BMP4 to the anterior primitive streak induction stage facilitated the OSR1$^+$GATA3$^+$ cell induction. Scale bars, 100 µm.

FIG. 1G The effects of adding BMP4 and LDN193189 to the induction stages of anterior primitive streak (APS) and anterior intermediate mesoderm (Anterior IM) on the differentiation of OSR1$^+$GATA3$^+$ cells. Immunostaining analysis for OSR1 (GFP, green) and GATA3 (red). While adding LDN193189 to the anterior intermediate mesoderm induction stage did not change the induction efficiency of OSR1$^+$ GATA3$^+$ cells, the addition of BMP4 inhibited the differentiation. Scale bars, 100 µm.

Figure 1H:
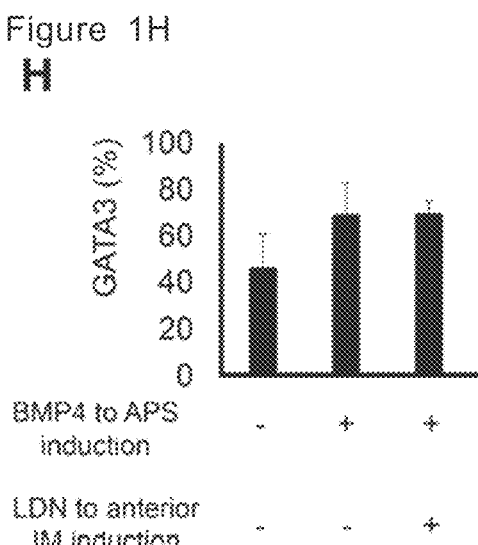

FIG. 1H The effects of adding BMP4 and LDN193189 to the induction stages of anterior primitive streak (APS) and anterior intermediate mesoderm (Anterior IM) on the differentiation of OSR1$^+$GATA3$^+$ cells. The induction rates of GATA3$^+$ cells by treatment without BMP4 at the anterior primitive streak induction stage or LDN193189 at the anterior intermediate mesoderm induction stage was 46.3±14.8%. The induction rates of GATA3$^+$ cells by treatment with BMP4 at the anterior primitive streak stage but without LDN193189 at the anterior intermediate mesoderm stage was 69.1±13.9%. The induction rates of GATA3$^+$ cells by treatment with BMP4 at the anterior primitive streak stage and LDN193189 at the anterior intermediate mesoderm stage was 69.6±5.7%. The data from four independent experiments are presented as the mean±s.d. (n=4).

Figure 2A:
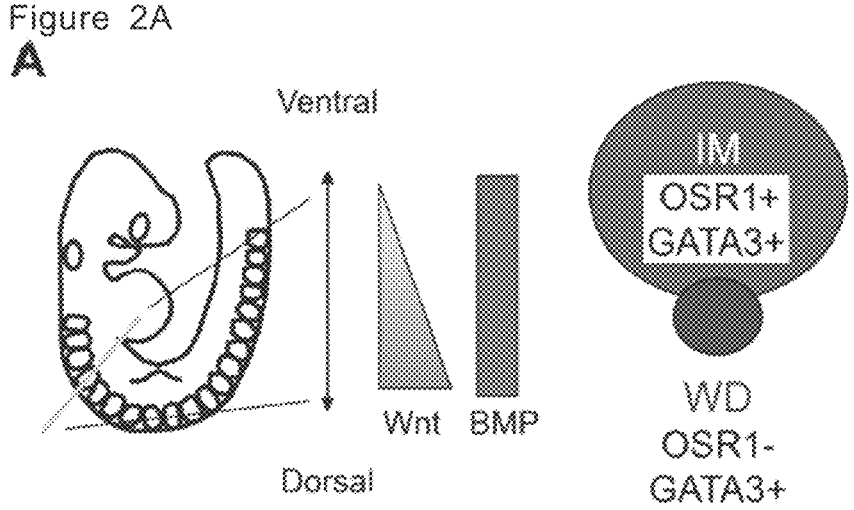

FIG. 2A Schematic of the concentration gradients of Wnt and BMP signals across the dorsal-ventral axis in E8.5-9 mouse embryos. Wnt and BMP proteins are secreted from surface ectoderm (dorsal) and BMPs are also secreted from lateral plate mesoderm (ventral). Wolffian duct (WD; OSR1$^-$ GATA3$^+$) is formed dorsally against anterior intermediate mesoderm (IM; OSR1$^+$GATA3$^+$).

Figure 2B:
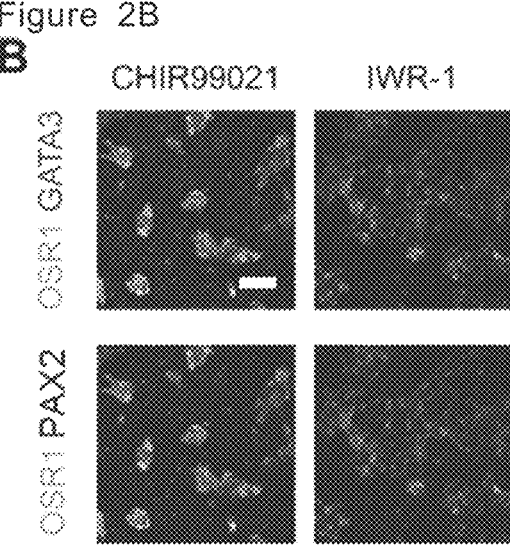

FIG. 2B Immunostaining analysis for OSR1 (GFP, green), GATA3 (red) and PAX2 (purple). Adding CHIR99021 to anterior intermediate mesoderm cells enhanced the differentiation of OSR1$^-$GATA3$^+$PAX2$^+$ Wolffian duct cells (left), while adding IWR-1 inhibited the Wolffian duct induction (right). Scale bar, 100 µm. 3D45 cells were used.

Figures 2C, 2D:
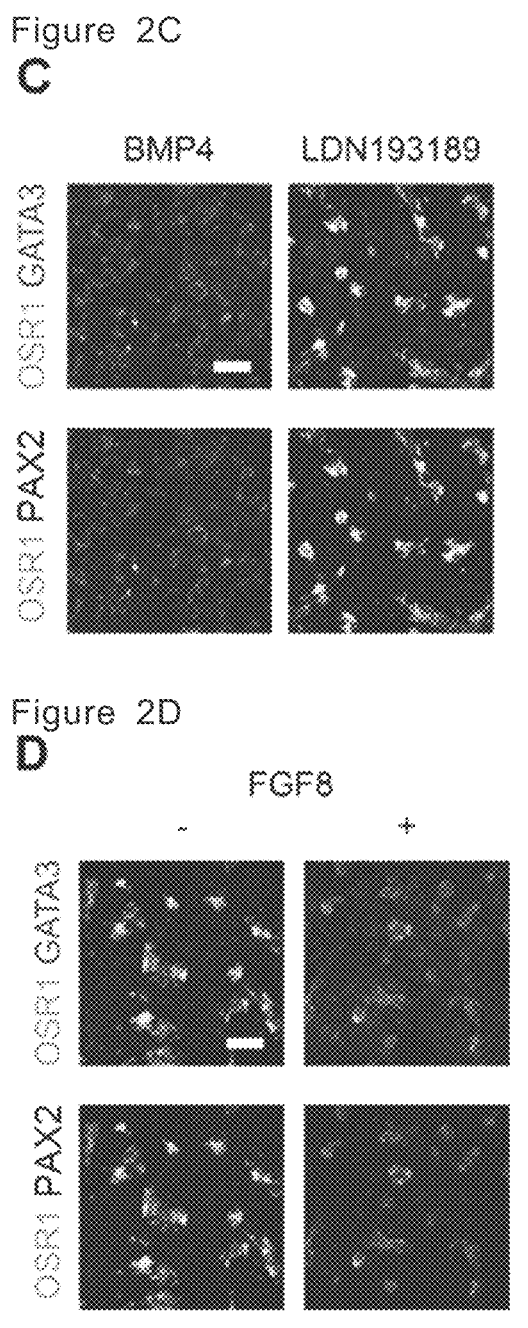

FIG. 2C Immunostaining analysis for OSR1 (GFP, green), GATA3 (red) and PAX2 (purple). Adding BMP4 to anterior intermediate mesoderm cells inhibited the differentiation of Wolffian duct cells (left), while adding LDN193189 enhanced the Wolffian duct induction (right). Scale bar, 100 µm. 3D45 cells were used.

FIG. 2D Immunostaining analysis for OSR1 (GFP, green), GATA3 (red) and PAX2 (purple). Treatment of anterior intermediate mesoderm cells with CHIR99021 and LDN193189 induced Wolffian duct cells (left). Adding FGF8 to the treatment enhanced the Wolffian duct induction (right). Scale bar, 100 µm. 3D45 cells were used.

FIG. 2E Total cell numbers before and after treatment with FGF8 alone, GDNF alone and a combination of FGF8 and GDNF are 1.44±0.29×10$^5$/cm, 4.69±0.65×10$^5$/cm$^2$, 2.37±0.56×10$^5$/cm$^2$ and 5.44±0.54×10$^5$/cm$^2$, respectively. The data from three independent experiments are presented as the mean±s.d. (n=3). 3D45 cells were used.

FIG. 2F Immunostaining analysis for Ki67 and GATA3. Scale bar, 100 µm. KhES3 cells were used.

FIG. 2G Immunostaining analysis for Ki67, GATA3 and RET. Scale bar, 100 µm. 3D45 cells were used.

FIG. 2H Immunostaining analysis for Wolffian duct markers. Scale bar, 100 µm. 3D45 cells were used.

FIG. 3A Morphological changes during the first 2 days of an aggregate formed from 1×10$^4$ dissociated cells. Scale bars, 300 µm. 511-3E cells were used.

FIG. 3B Immunostaining analysis of the aggregate on day 2 for GATA3 (red) and E-CADHERIN (green). Note that cells negative for mature Wolffian duct markers are separated from Wolffian duct cells in the aggregate. Scale bar, 300 µm. 511-3E cells were used.

FIG. 3C Morphology of a day 2 aggregate before and after pipetting to remove non-Wolffian duct cells. The arrow and arrowhead in middle panel indicates separated Wolffian duct and non-Wolffian duct cells, respectively. Scale bar, 300 µm. 511-3E cells were used.

FIG. 3D Immunostaining analysis of day 2 aggregates after removing non-Wolffian duct cells for Wolffian duct markers. Scale bar, 100 µm. 511-3E cells were used.

FIG. 3E Morphological changes during the first 7 days of a mature Wolffian duct aggregate after pipetting and embedded in Matrigel. Scale bar, 300 µm. 511-3E cells were used.

FIG. 3F 3D imaging of a day 7 structure generated from 511-3E cells. 511-3E cells were used.

Figures 3G, 3H:
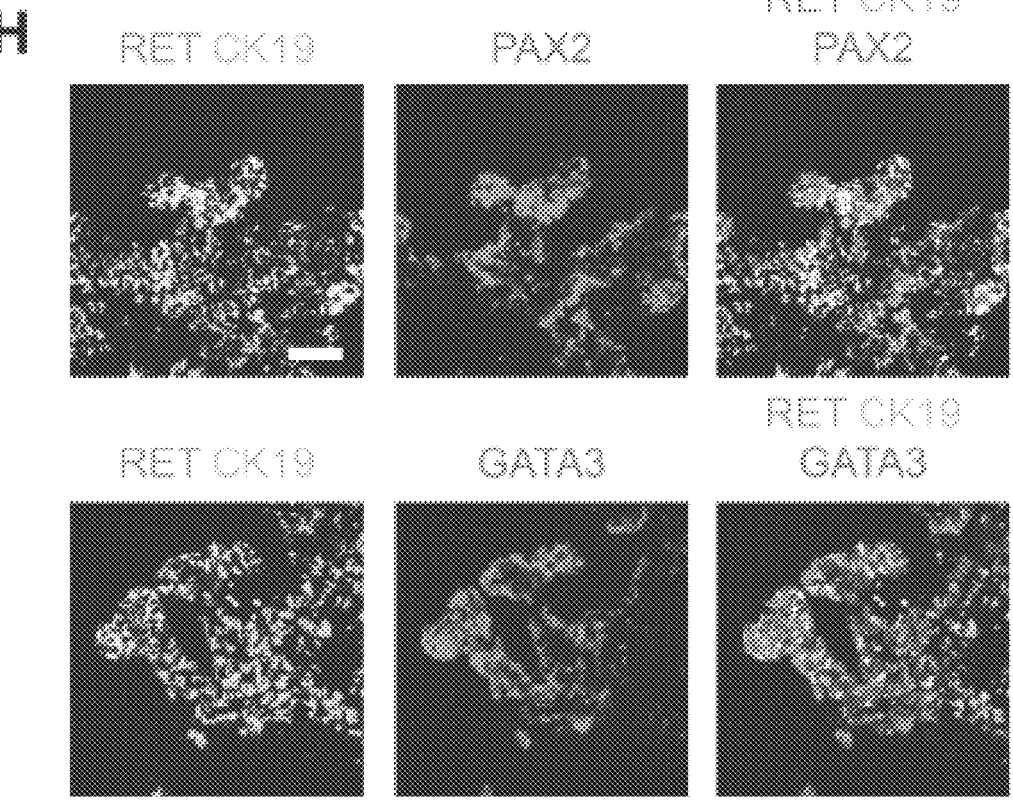

FIG. 3G Immunostaining analysis of a day 9 structure for ureteric bud markers. Scale bar, 100 µm. 3D45 cells were used.

FIG. 3H Immunostaining analysis of day 15 structures for an ureteric bud trunk marker, CK19 (red), an ureteric bud tip marker, RET (green), and common ureteric bud markers, PAX2 and GATA3 (blue). Scale bar, 100 µm. 3D45 cells were used.

FIG. 4 Directed differentiation protocol from hPSCs into branching ureteric bud tissues. APS, anterior primitive streak; Anterior IM, anterior intermediate mesoderm; WD, Wolffian duct; UB, ureteric bud. Y, 10 µM Y-27632; A, 100 ng/ml Activin A; C3, 3 µM CHIR99021; B, 10 ng/ml BMP4; F8, 200 ng/ml FGF8; TT, 0.1 µM TTNPB; A83, 1 µM A83-01; LDN, 0.1 µM LDN193189; C1, 1 µM CHIR99021; G, 100 ng/ml GDNF; F1, 200 ng/ml FGF1; Tzv, 10 µM Thiazovivin.

FIG. 5A Schematic of the differentiation from hiPSCs through anterior primitive streak (APS) and presomitic mesoderm (PSM) cells into early somite.

FIG. 5B Immunostaining analysis for BRACHYURY (red) indicating the differentiation from hiPSCs into anterior primitive streak (APS) cells. Scale bar, 100 µm.

FIG. 5C Immunostaining analysis for TBX6 (red) indicating the differentiation from anterior primitive streak (APS) into presomitic mesoderm (PSM) cells. Scale bar, 100 µm.

FIG. 5D Immunostaining analysis for PAX3 (red) indicating the differentiation from presomitic mesoderm (PSM) into early somite cells. Scale bar, 100 µm.

FIG. 5E Induction of presomitic mesoderm (PSM) into nephron progenitor (NP) cells with 10 ng/ml Activing A, 3 ng/ml BMP4, 3 μM CHIR99021, 0.1 μM TTNPB and 10 μM Y-27632, followed by treatment with 5 ng/ml FGF9, 1 μM CHIR99021 and 10 μM Y-27632. Immunostaining analysis for OSR1 (GFP, green) and SIX2 (red) indicates the differentiation from presomitic mesoderm into nephron progenitor cells. Scale bar, 100 μm.

FIG. 5F Double immunostaining analysis for OSR1 (GFP, green) and SOX17 (purple) indicating that treatment with 1 μM A83-01 decreases the differentiation into definitive endoderm cells without inhibiting the induction of anterior intermediate mesoderm-like cells. Scale bar, 100 μm.

Figures 6, 7A, 7B:
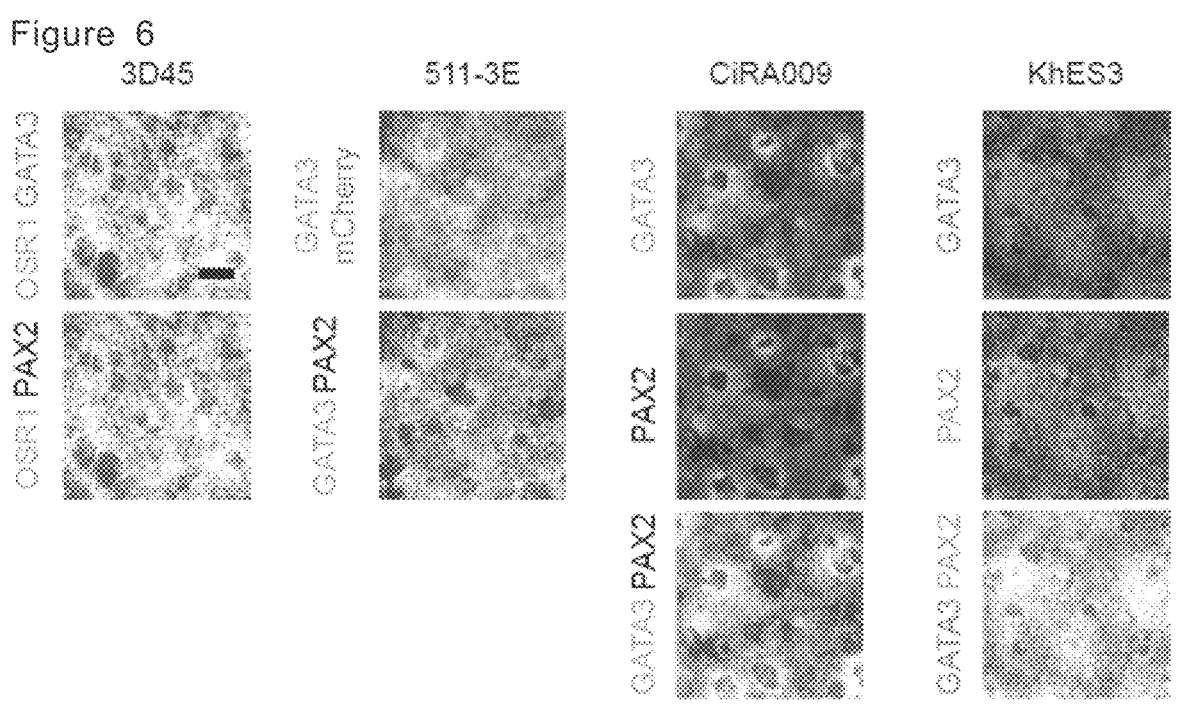

FIG. 6 Induction of anterior intermediate mesoderm cells from multiple hiPSC/ESC lines. Immunostaining analyses for anterior intermediate mesoderm markers on differentiated cells on day 4 from an OSR1-GFP knock-in hiPSC line (3D45) (OSR1-GFP, green; GATA3, red; PAX2, purple), an hiPSC line constitutively expressing mCherry (511-3E) (GATA3, green; mCherry, red; PAX2, purple), an hiPSC line established from an ADPKD patient (CiRA00009) (GATA3, green; PAX2, purple), and an hESC line (KhES3) (GATA3, red; PAX2, green).

FIG. 7A Immunostaining analysis for Wolffian duct markers, LHX1, GATA3, RET, CK8 and PAX2, on differentiated cells on day 7 from KhES3 cells. Scale bar, 100 μm.

FIG. 7B Immunostaining analysis on differentiated cells on day 7 from 3D45 cells for FOXF1$^+$ lateral plate mesoderm, OSR1$^+$PAX2$^-$ posterior intermediate mesoderm, PAX3$^+$ early somite and PAX6$^+$ neural ectoderm cells indicated partial differentiation of posterior intermediate mesoderm and neural ectoderm except for anterior intermediate mesoderm. Scale bar, 100 μm.

Figure 8A:
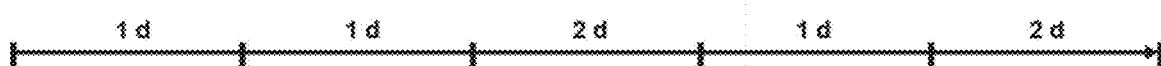

FIG. 8A Directed differentiation protocol from hPSCs into early Wolffian duct cells. Anterior PS, anterior primitive streak; Anterior IM, anterior intermediate mesoderm; ND, Wolffian duct.

Figure 8B:
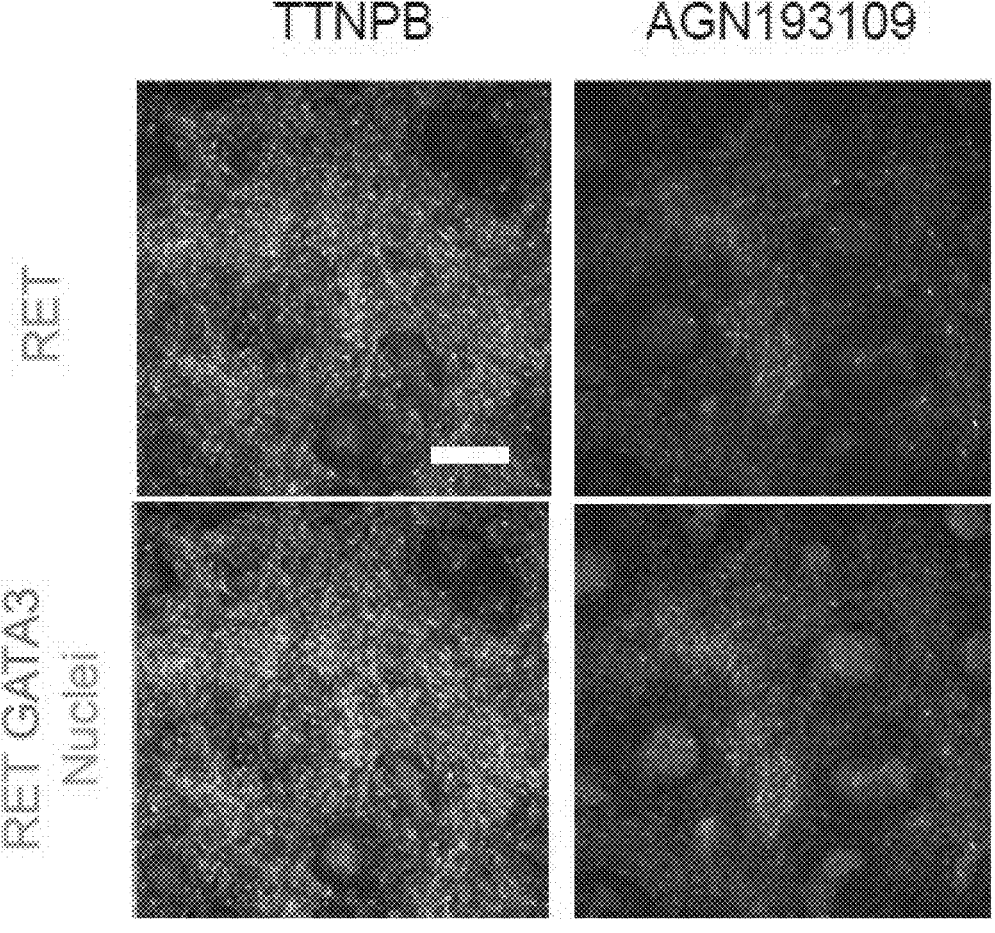

FIG. 8B Immunostaining analysis for RET (green) and GATA3 (red) when adding TTNPB (left) or AGN193109 (right) to anterior intermediate mesoderm cells. Adding AGN193109 decreased the expression of RET, a Wolffian duct cell marker. Scale bar, 100 μm.

Figures 9A, 9B:
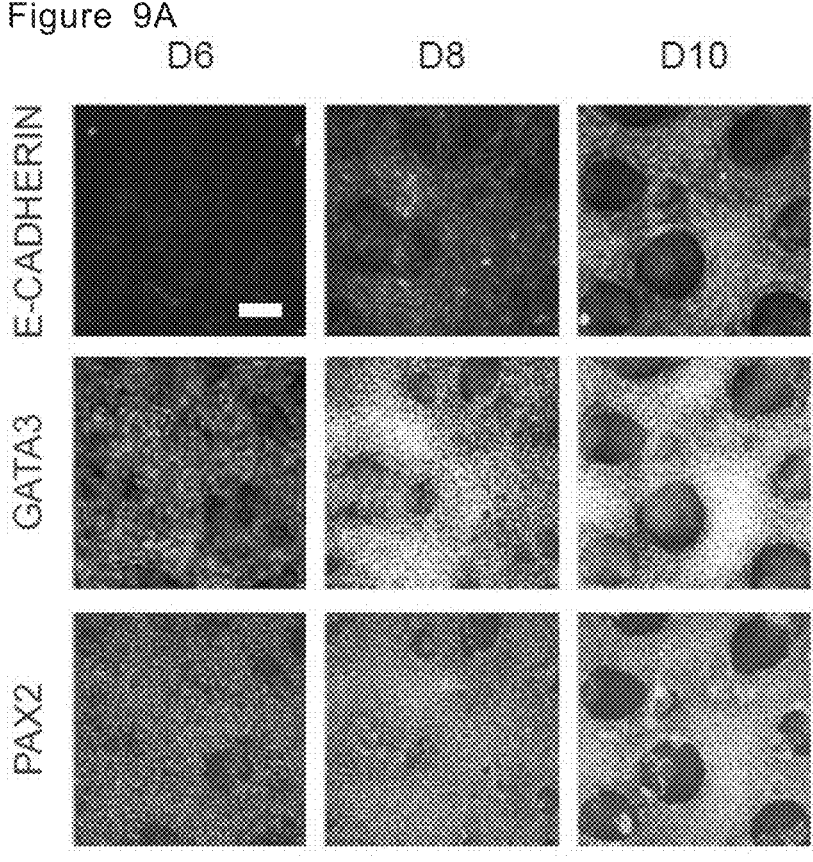

FIG. 9A Immunostaining analysis for Wolffian duct cell markers 6, 8 and 10 days after inducing Wolffian duct cells from anterior intermediate mesoderm cells. Scale bar, 100 μm.

FIG. 9B Improved directed differentiation protocol from hPSCs into mature Wolffian duct aggregates. Anterior PS, anterior primitive streak; Anterior IM, anterior intermediate mesoderm; ND, Wolffian duct.

FIG. 9C Immunostaining analysis of day 2 aggregates before and after removing non-Wolffian duct cells for Wolffian duct cell markers. Scale bar, 300 μm.

FIG. 10A Improved directed differentiation protocol from hPSCs into ureteric bud tissues. Anterior PS, anterior primitive streak; Anterior IM, anterior intermediate mesoderm; ND, Wolffian duct; UB, ureteric bud.

FIG. 10B Budding of a polarized ureteric bud from a Wolffian duct epithelial cell mass.

FIG. 10C Morphological changes during the first 4 days of a mature Wolffian duct aggregate in Matrigel-containing medium.

FIG. 10D Immunostaining analysis for PAX2 (green), LAMININ (red), and EZRIN (white) indicating the generation of a polarized ureteric bud.

FIG. 11A Protocol for cryopreserving early Wolffian duct cells induced from hPSCs. Anterior PS, anterior primitive streak; Anterior IM, anterior intermediate mesoderm; ND, Wolffian duct.

FIG. 11B Immunostaining analysis of aggregates after removing non-Wolffian duct cells from the cell mass generated from the cells cryopreserved and then thawed. Scale bar, 300 μm.

FIG. 12A Protocol for inducing the differentiation into ureteric bud tissues from hPSCs and generating ureteric bud organoids from isolated ureteric bud tissues. Anterior PS, anterior primitive streak; Anterior IM, anterior intermediate mesoderm; ND, Wolffian duct; UB, ureteric bud.

FIG. 12B Schematic diagram showing the progression of branching of a ureteric bud tissue isolated from a mature Wolffian duct cell aggregate.

FIG. 12C Morphological changes during the first 10 days of a ureteric bud tissue mechanically isolated from a mature Wolffian duct cell aggregate and then cultured in Matrigel-containing medium under a suspension culture condition.

FIG. 12D Immunostaining analysis of a day 14 structure for PAX2 (green) and CK8 (red).

FIG. 12E Immunostaining analysis of a day 14 structure for PAX2 (blue), RET (green) and CK8 (red).

FIG. 12F Immunostaining analysis of a day 14 structure for PAX2 (purple), EZRIN (green) and LAMININ (red).

FIG. 13A Protocol for inducing the differentiation into ureteric bud tissues from hPSCs and maintaining ureteric bud organoids. Anterior PS, anterior primitive streak; Anterior IM, anterior intermediate mesoderm; ND, Wolffian duct; UB, ureteric bud.

Figures 13B, 13C:
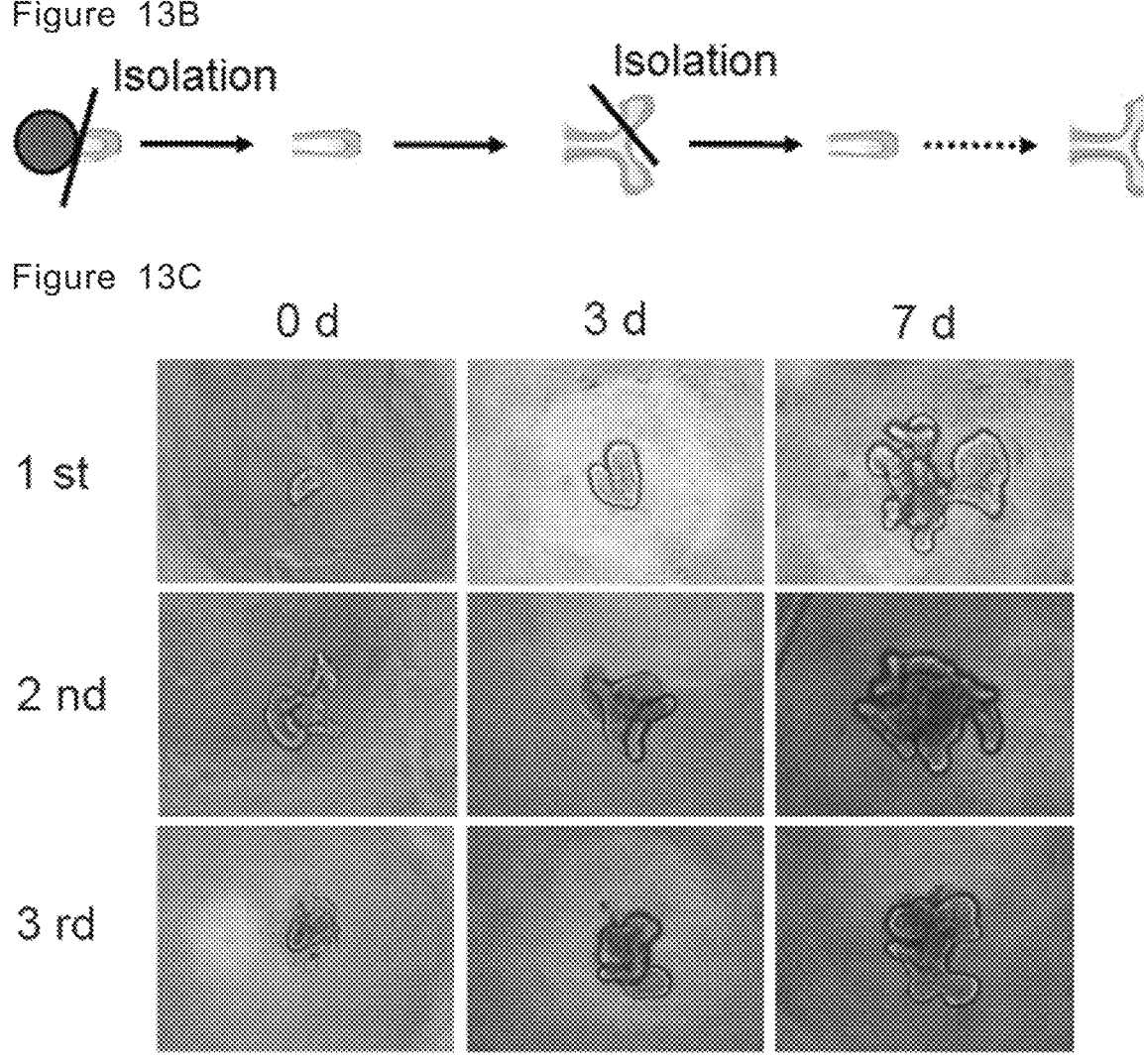

FIG. 13B Schematic diagram showing that ureteric bud organoids can be maintained by truncating the tip region of a ureteric bud organoid and then culturing the tip region.

FIG. 13C Morphological changes during the first 7 days of the tip region of a ureteric bud tissue (ureteric bud tip tissue) truncated from a ureteric bud organoid of the first, second or third generation.

FIG. 14A Protocol for expansion-culturing ureteric bud tip tissues using ureteric bud tissues induced from hPSCs. Anterior PS, anterior primitive streak; Anterior IM, anterior intermediate mesoderm; ND, Wolffian duct; UB, ureteric bud.

Figure 14B:
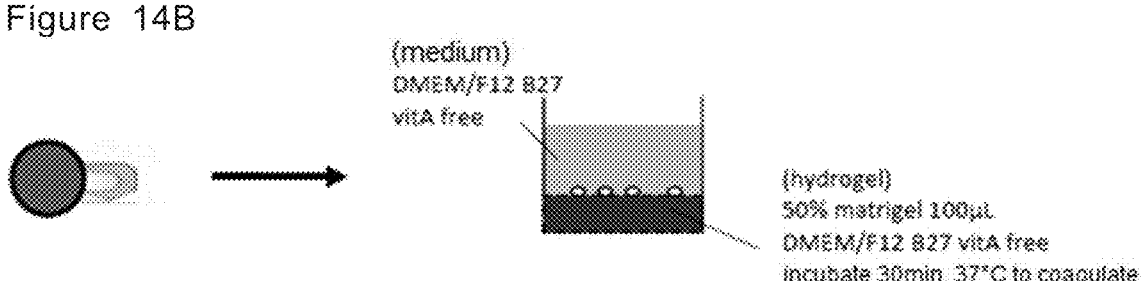

FIG. 14B Schematic diagram showing that a ureteric bud tissue with a mature Wolffian duct cell aggregate is dissociated into single cells and then the single cells are cultured on hydrogel under a three-dimensional culture condition.

Figure 14C:
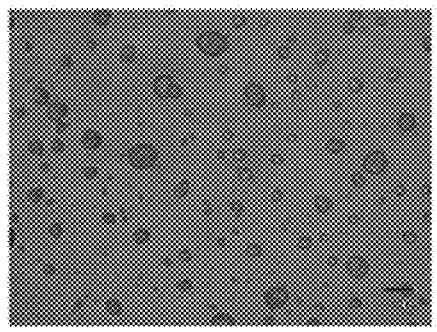

FIG. 14C Microscopic image of day 7 structures.

Figure 14D:
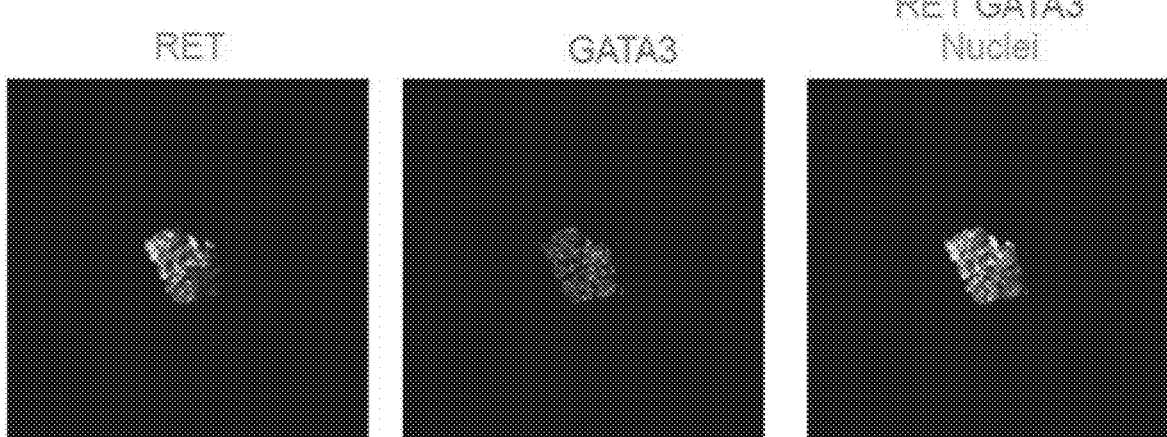

FIG. 14D Immunostaining analysis of a day 7 structure for RET (green) and GATA3 (red).

FIG. 15A Protocol for generating ureteric bud organoids from expansion-cultured ureteric bud tip tissues. Anterior PS, anterior primitive streak; Anterior IM, anterior intermediate mesoderm; ND, Wolffian duct; UB, ureteric bud.

Figures 15B, 15C, 15D, 16A:
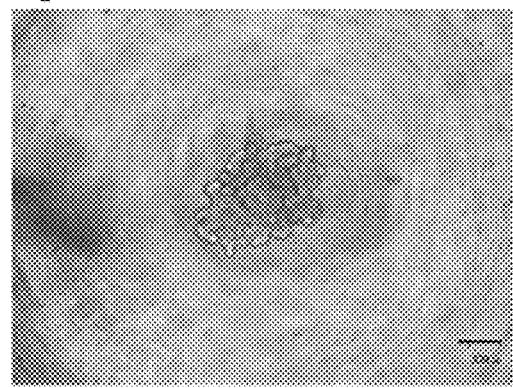

FIG. 15B Schematic diagram showing that a ureteric bud tissue with a mature Wolffian duct cell aggregate is dissociated into single cells, the single cells are cultured on hydrogel under a three-dimensional culture condition, and then the cells are cultured in Matrigel-containing medium under a suspension culture condition.

FIG. 15C Microscopic image of a day 14 structure.

FIG. 15D Immunostaining analysis of a day 14 structure for EZRIN (green), LAMININ (red), CK8 (green) and GATA3 (red).

FIG. 16A Directed differentiation protocol into collecting duct progenitor cells.

Figure 16B:
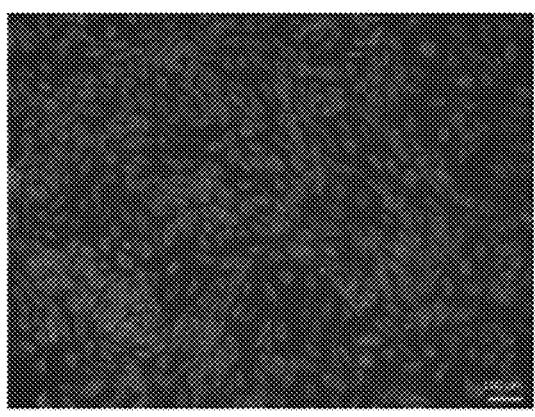

FIG. 16B Immunostaining analysis for aquaporin 2 (AQP2; red) indicating the differentiation into collecting duct progenitor cells.

EMBODIMENTS FOR CONDUCTING THE INVENTION

In the specification and claims of the present application, when a numerical value is accompanied with the term "about", the value is intended to include any value within the range of ±30%, ±20%, or ±10% of that value.

In the specification and claims of the present application, the expression "specific type of cell" means a cell group containing the type of cell unless otherwise specified, and the cell group may include cells other than the specified type of cell. For example, the expression "culture of a specific type of cell" means a culture of a cell group containing the type of cell, and may include cells other than the specified type of cell. Likewise, the expression "aggregate of a specific type of cell" means a cell aggregate containing the type of cells unless otherwise specified, and the cell aggregate may include cells other than the specified type of cells.

In the specification and claims of the present application, "pluripotent stem cells" refer to stem cells which have pluripotency, that is the ability of cells to differentiate into all types of the cells in the living body, as well as proliferative capacity. Examples of the pluripotent stem cells include embryonic stem (ES) cells (J. A. Thomson et al., (1998), Science 282: 1145-1147; J. A. Thomson et al., (1995), Proc. Natl. Acad. Sci. USA, 92: 7844-7848; J. A. Thomson et al., (1996), Biol. Reprod., 55: 254-259; J. A. Thomson and V. S. Marshall (1998), Curr. Top. Dev. Biol., 38: 133-165), embryonic stem cells derived from cloned embryo obtained by nuclear transfer (ntES cells) (T. Wakayama et al., (2001), Science, 292: 740-743; S. Wakayama et al., (2005), Biol. Reprod., 72: 932-936; J. Byrne et al., (2007), Nature, 450: 497-502), germline stem cells ("GS cells") (M. Kanatsu-Shinohara et al., (2003) Biol. Reprod., 69: 612-616; K. Shinohara et al., (2004), Cell, 119: 1001-1012), embryonic germ cells ("EG cells") (Y. Matsui et al., (1992), Cell, 70: 841-847; J. L. Resnick et al., (1992), Nature, 359: 550-551), induced pluripotent stem (iPS) cells (K. Takahashi and S. Yamanaka (2006) Cell, 126: 663-676; K. Takahashi et al., (2007), Cell, 131:861-872; J. Yu et al., (2007), Science, 318: 1917-1920; Nakagawa, M. et al., Nat. Biotechnol. 26: 101-106 (2008); WO 2007/069666), pluripotent cells derived from cultured fibroblasts and bone marrow stem cells (Muse cells) (WO 2011/007900). Mouse or human pluripotent stem cells, particularly ES cells and iPS cells are preferably used.

"ROCK inhibitor" is not particularly limited as long as it can suppress the function of Rho-kinase (ROCK), and examples of ROCK inhibitors include Y-27632 (for example, see Ishizaki et al., Mol. Pharmacol. 57, 976-983 (2000); Narumiya et al., Methods Enzymol. 325, 273-284 (2000)), Fasudil/HA1077 (for example, see Uenata et al., Nature 389: 990-994 (1997)), SR3677 (for example, see Feng Y et al., J Med Chem. 51: 6642-6645 (2008)), GSK269962 (for example, see Stavenger R A et al., J Med Chem. 50: 2-5 (2007) or WO 2005/037197), H-1152 (for example, see Sasaki et al., Pharmacol. Ther. 93: 225-232 (2002)), Wf-536 (for example, see Nakajima et al., Cancer Chemother Pharmacol. 52 (4): 319-324 (2003)) and derivatives thereof, as well as an antisense nucleic acid against ROCK, an RNA interference-inducing nucleic acid (for example, an siRNA) against ROCK, a dominant negative mutant of ROCK, and expression vectors for them. In addition, as the ROCK inhibitor, other known low molecular weight compounds may be used (for example, see U.S. patent publications Nos. 2005/0209261, 2005/0192304, 2004/0014755, 2004/0002508, 2004/0002507, 2003/0125344 and 2003/0087919, as well as International Publications Nos. WO 2003/062227, WO 2003/059913, WO 2003/062225, WO 2002/076976, and WO 2004/039796). In the present application, one or more kinds of ROCK inhibitors may be used. The ROCK inhibitors which are preferably used include Y-27632, Fasudil/HA1077, SR3677, GSK269962 and H-1152.

"Activator of activin receptor-like kinase-4,7" is a substance that activates ALK-4 and/or ALK-7. An activin is preferable and Activin A is more preferable.

"GSK3β inhibitor" is defined as a substance which inhibits the kinase activity of a GSK3β protein such as an ability to phosphorylate β-catenin, and many GSK3β inhibitors are known. Examples of the GSK3β inhibitors include BIO (also called GSK-33 inhibitor IX; 6-bromoindirubin3'-oxime) which is a derivative of indirubin, SB216763 (3-(2,4-dichlorophenyl)-4-(1-methyl-1H-indol-3-yl)-1H-pyrrole-2,5-dione) and SB415286 (3-[(3-chloro-4-hydroxyphenyl)amino]-4-(2-nitrophenyl)-1H-pyrrole-2,5-dione) which are derivatives of maleimide, GSK-3β inhibitor VII (4-dibromoacetophenone) which is a phenyl α bromomethylketone compound, L803-mts (also called, GSK-3β peptide inhibitor; Myr-N-GKEAPPAPPQSpP-NH2) which is a cell-penetrating phosphorylated peptide, and CHIR99021 (6-[2-[4-(2,4-Dichlorophenyl)-5-(4-methyl-1H-imidazol-2-yl)pyrimidin-2-ylamino]ethylamino]pyridine-3-carbonitrile) which has high selectivity. These compounds are commercially and easily available, for example, from Calbiochem and Biomol. The GSK3β inhibitor used herein may preferably be CHIR99021.

FGF1 to FGF23 are known as "fibroblast growth factors". The fibroblast growth factor may be appropriately selected from them. FGF8 is preferably used in stages 2, 3, 4', 5', 6, 7 and 7' described below. FGF1 is preferably used in stages 4, 5 and 6', which are the stages for the maturation of Wolffian ducts, the induction of aggregates, and the induction of ureteric bud tissues after the induction of Wolffian duct cells, respectively.

"Retinoic acid receptor (RAR) agonist" may be naturally-occurring retinoid, chemically synthesized retinoid, a retinoic acid receptor agonist not having the retinoid structure, or a naturally occurring substance having the retinoic acid receptor agonist activity. Examples of naturally occurring retinoid having the retinoic acid receptor agonist activity include retinoic acid such as known stereoisomers, all-trans retinoic acid (all-trans RA) and 9-cis retinoic acid (9-cis RA). Chemically synthesized retinoid is known to the art (for example, U.S. Pat. Nos. 5,234,926 and 4,326,055). Examples of retinoic acid receptor agonists not having the retinoid structure include Am80, AM580, TTNPB, and AC55649. Examples of naturally occurring substances having the retinoic acid receptor agonist activity include honokiol and magnolol (Annual Report of Research Institute for Biological Function 9:55-61, 2009). The RAR agonist used in step 2 may preferably be retinoic acid, AM580 (4-[[5,6,7,8-tetrahydro-5,5,8,8-tetramethyl-2-naphthalenyl] carboxyamide] benzoic acid), TTNPB (4-[[E]-2-[5,6,7,8-tetrahydro-5,5,8,8-tetramethyl-2-naphthalenyl]-1-propenyl] benzoic acid), and AC55649 (4'-octyl-[1,1'-biphenyl]-4-carboxylic acid) and more preferably, TTNPB.

"TGFβ inhibitor" is a substance which inhibits the signal transduction starting from the binding of TGFβ to its receptor and leading to SMAD. The TGFβ inhibitor is not particularly limited as long as it inhibits the binding of TGFβ to the receptor, an ALK family protein, or inhibits phosphorylation of SMAD caused by the ALK family protein. Examples of TGFβ inhibitors include Lefty-1 (e.g. NCBI Accession Nos: NM_010094 (mouse), and NM_020997

(human)), SB431542 and SB202190 (R. K. Lindemann et al., Mol. Cancer, 2003, 2: 20), SB505124 (GlaxoSmithKline), NPC30345, SD093, SD908, SD208 (Scios), LY2109761, LY364947, LY580276 (Lilly Research Laboratories), A-83-01 (3-(6-Methyl-2-pyridinyl)-N-phenyl-4-(4-quinolinyl)-1H-pyrazole-1-carbothioamide, WO 2009/146408), ALK5 inhibitor II (2-[3-[6-methylpyridin-2-yl]-1H-pyrazol-4-yl]-1,5-naphthyridine), TGFβRI kinase inhibitor VIII (6-[2-tert-butyl-5-[6-methyl-pyridin-2-yl]-1H-imidazol-4-yl]-quinoxaline) and derivatives thereof. Preferably, the TGFβ inhibitor may be A-83-01.

Examples of "BMP inhibitors" include protein inhibitors such as Chordin, Noggin and Follistatin; Dorsomorphin 6-[4-(2-piperidin-1-yl-ethoxy)phenyl]-3-pyridin-4-yl-pyrazolo[1,5-a]pyrimidine and a derivative thereof (P. B. Yu et al. (2007), Circulation, 116: II_60, P. B. Yu et al. (2008), Nat. Chem. Biol., 4:33-41, J. Hao et al. (2008), PLoS ONE, 3 (8): e2904), and LDN-193189 (4-(6-(4-(piperazin-1-yl)phenyl) pyrazolo[1,5-a]pyrimidin-3-yl)quinoline). Preferable BMP inhibitor is LDN-193189.

"Wnt signal inhibitor" is not particularly limited as long as it inhibits a signaling pathway via Wnt. Examples of Wnt signal inhibitors include IWR-1, IWP-2, IWP-3, IWP-4, 2-(4-trifluoromethylphenyl)-7,8-dihydro-5H-thiopyrano[4, 3-d]pyrimidin-4(3H)-one (XAV939), G-CSF, IGFBP4, Dkk1, Cerberus, anti-Wnt antibody, Wnt agonist (Wnt receptor inhibitor), soluble Wnt receptor proteins such as Frzb-1, and dominant negative form. Preferable Wnt signal inhibitor is IWR-1.

In each step of the methods in the present application, the cells may be cultured at a temperature of about 30-40° C., preferably about 37° C. under a $CO_2$-containing air atmosphere, but not limited to such conditions. The concentration of $CO_2$ in the air may preferably be about 2-5%.

Prior to the method of the present application, pluripotent stem cells are cultured in a culture vessel preferably coated for pluripotent stem cell culture, e.g. with laminin or commercially available iMatrix silk, in a maintenance medium for pluripotent stem cells supplemented with a ROCK inhibitor for 12 to 48 hours, e.g. about 24 hours. A commercially available medium can be appropriately used as the maintenance medium for pluripotent stem cells. Examples of the maintenance medium for pluripotent stem cells include StemFit© AK02N medium (Ajinomoto Co., Inc.). When Y-27632 is used as a ROCK inhibitor, its concentration in the medium is 0.1 μM to 1 mM, preferably 1 μM to 100 μM, more preferably 5 μM to 20 μM, and for example about 10 μM.

Next, the differentiation of pluripotent stem cells is induced by the method of the present application. The medium can be prepared by appropriately adding factors necessary for each stage to a basal medium used for culturing animal cells. Examples of the basal media include MEM Zinc Option Medium, IMEM Zinc Option Medium, IMDM Medium, Medium 199 Medium, Eagle's Minimum Essential Medium (EMEM) Medium, α-MEM Medium, Dulbecco's modified Eagle's Medium (DMEM) Medium, DMEM/F12 Medium, Ham's F12 Medium, RPMI 1640 Medium, Fischer's Medium, and mixtures of these media. The basal medium may contain serum (for example, fetal bovine serum (FBS)) or the basal medium may be a serum-free medium. As required, the basal medium may contain, for example, one or more alternatives to sera such as albumin, transferrin, KnockOut Serum Replacement (KSR) (Thermo Fisher Scientific), which is an alternative to serum used for culturing ES cells, N2 Supplement (Thermo Fisher Scientific), B-27 Supplement (Thermo Fisher Scientific), a fatty acid, insulin, a collagen precursor, a trace element, 2-mercaptoethanol, and 3'-Thioglycerol, and the basal medium may also contain one or more substances such as a lipid, an amino acid, L-glutamine, GlutaMAX (Thermo Fisher Scientific), a nonessential amino acid (NEAA), a vitamin, a growth factor, an antibiotic, an antioxidant, pyruvic acid, a buffer agent, an inorganic salt, and equivalents thereof as well as one or more other substances normally added to a medium used for culturing animal cells.

In one embodiment, the basal medium in each step of the method of the present application except for stage 6' may be Essential 6™ medium (Thermo Fisher Scientific Inc), which is serum-free DMEM/F12 medium supplemented with L-ascorbic acid-2-phosphate magnesium, sodium selenium, insulin, $NaHCO_3$ and transferrin. In one embodiment, the basal medium in stage 6' of the method of the present application may be DMEM/F12 B27 vitA free medium.

Hereinafter, each stage of the method of the present application is described. In each stage, the induction of the cells of interest can be confirmed by the expressions of markers on the cells. The expression of a marker can be confirmed by a known method such as immunostaining and FACS.

Stage 1

Stage 1 of the present application is the step of inducing anterior primitive streak cells from pluripotent stem cells. In this step, the pluripotent stem cells are cultured in the presence of an activator of activin receptor kinase 4,7 and a GSK3 inhibitor under a two-dimensional culture condition. Preferably, BMP4 is further present.

When Activin A is used as an activator of activin receptor kinase 4,7, its concentration in the medium is generally 1 ng/ml to 10 μg/ml, preferably 10 ng/ml to 1 μg/ml, more preferably 50 ng/ml to 200 ng/ml, and for example about 100 ng/ml.

When CHIR99021 is used as a GSK3B inhibitor, its concentration in the medium is generally 0.03 μM to 300 μM, preferably 0.3 μM to 30 μM, more preferably 1.5 μM to 6 μM, and for example about 3 μM.

The concentration of BMP4 in the medium is 0.1 ng/ml to 1 μg/ml, preferably 1 ng/ml to 100 ng/ml, more preferably 5 ng/ml to 20 ng/ml, and for example about 10 ng/ml.

In stage 1, the cells may preferably be cultured in a plate for culturing pluripotent stem cells with replacing the medium. The culture period is from 12 to 48 hours, for example, about 24 hours. The generation of anterior primitive streak (APS) cells can be confirmed by the expression of BRACHYURY in the cells.

Stage 2

Stage 2 of the present application is the step of inducing anterior intermediate mesoderm (anterior IM) cells from anterior primitive streak cells. The anterior primitive streak cells may be obtained in stage 1 or by another known method.

In this step, the anterior primitive streak cells are cultured in the presence of a fibroblast growth factor, a retinoic acid receptor agonist, a TGFβ inhibitor and a BMP inhibitor under a two-dimensional culture condition.

When FGF8 is used as a fibroblast growth factor, its concentration in the medium is generally 2 ng/ml to 20 μg/ml, preferably 20 ng/ml to 2 μg/ml, more preferably 100 ng/ml to 400 ng/ml, and for example about 200 ng/ml.

When TTNPB is used as a retinoic acid receptor agonist, its concentration in the medium is generally 0.001 μM to 10 μM, preferably 0.01 μM to 1 μM, more preferably 0.05 μM to 0.2 μM, and for example about 0.1 μM.

When A83-01 is used as a TGFβ inhibitor, its concentration in the medium is generally 0.01 μM to 100 μM, preferably 0.1 μM to 10 μM, more preferably 0.5 μM to 2 μM, and for example about 1 μM.

When LDN-193189 is used as a BMP inhibitor, its concentration in the medium is generally 0.001 μM to 10 μM, preferably 0.01 μM to 1 μM, more preferably 0.05 μM to 0.2 μM, and for example about 0.1 μM.

In stage 2, the culture is performed for a total of 2 to 6 days, preferably about 3 to about 4 days. In the first half of stage 2, for example, for about 2 days, the cells may be cultured by replacing the medium of the cell culture obtained in stage 1 or by another method with the medium for stage 2. In the second half of stage 2, for example, for about one day, the culture plate is replaced with a cell culture plate coated with a thin layer of extracellular matrix proteins such as Matrigel and the cells are then cultured. After replacing the cell culture plate, a ROCK inhibitor, for example, Y-27632, is preferably added to the medium and the culture is continued. The concentration of Y-27632 in the medium may be the same as that used for culturing pluripotent stem cells before stage 1.

The generation of anterior intermediate mesoderm cells can be confirmed, for example, by the expression of OSR1 and GATA3 in the cells. The expressions of PAX2, LHX1 and HOXB4, which are other markers for an intermediate mesoderm cell, may be confirmed alone or in combination.

Stage 3

Stage 3 of the present application is the step of inducing early Wolffian duct cells from anterior intermediate mesoderm cells. The anterior intermediate mesoderm cells are the cells obtained in stage 2.

In this step, the anterior intermediate mesoderm cells are cultured in the presence of a GSK3β inhibitor, a BMP inhibitor, a fibroblast growth factor and a glial cell line-derived neurotrophic factor (GDNF) under a two-dimensional culture condition. In this step, the medium may further contain a retinoic acid receptor agonist.

When CHIR99021 is used as a GSK3β inhibitor, its concentration in the medium is 0.01 μM to 100 μM, preferably 0.1 μM to 10 μM, more preferably 0.5 μM to 2 μM, and for example about 1 μM.

When LDN-193189 is used as a BMP inhibitor, its concentration in the medium is generally 0.001 μM to 10 μM, preferably 0.01 μM to 1 μM, more preferably 0.05 μM to 0.2 μM, and for example about 0.1 μM.

When FGF8 is used as a fibroblast growth factor, its concentration in the medium is generally 2 ng/ml to 20 μg/ml, preferably 20 ng/ml to 2 μg/ml, more preferably 100 ng/ml to 400 ng/ml, and for example about 200 ng/ml.

The concentration of a glial cell line-derived neurotrophic factor (GDNF) in the medium is generally 1 ng/ml to 10 μg/ml, preferably 10 ng/ml to 1 μg/ml, and for example about 100 ng/ml.

When TTNPB is used as a retinoic acid receptor agonist, its concentration in the medium is generally 0.001 μM to 10 μM, preferably 0.01 μM to 1 μM, more preferably 0.05 μM to 0.2 μM, and for example about 0.1 μM.

In stage 3, the cells may be cultured using a cell culture plate coated with extracellular matrix proteins such as Matrigel™, as in the second half of stage 2. The culture period may be from 24 hours to about 4 days, for example, about 48 hours.

The generation of early Wolffian duct cells can be confirmed by the expression of GATA3 without OSR1 in the cells. The expressions of PAX2, LHX1 and Cytokeratin 8, which are other Wolffian duct markers, may be further examined.

The early Wolffian duct cells obtained in this step can be cryopreserved. The cells can be frozen and thawed by using known methods. An Example of a method for freezing the cells comprises washing the early Wolffian duct cells obtained in stage 3 with PBS, dissociating the cells from a cell culture plate with cell dissociation solution such as Accutase, and removing the supernatant by centrifugation. Then, suspending the cells in cryopreservation solution such as stem cell banker, slowly freezing the cell suspension at −80° C. for 24 hours, and storing it at −196° C. (in liquid nitrogen). A freezing solution containing DMSO may be used as the cryopreservation solution. Specifically, examples of cryopreservation solutions include CELLBANKER (Nippon Zenyaku Kogyo Co., Ltd.), Bambanker (Nippon Genetics Co., Ltd.), TC-Protector (DS Pharma Biomedical Co., Ltd.), and CP-1 (Kyokuto Pharmaceutical Industrial Co., Ltd.). An example of a method of thawing frozen cells comprises rapidly thawing frozen early Wolffian duct cells, for example, in a warm bath at 37° C., washing out the cryopreservation solution using centrifugation, and suspending the cells in a medium. The early Wolffian duct cells cryopreserved and thawed by the method of the present application can be used as early Wolffian duct cells in the following embodiments.

Stage 4

Stage 4 is the step of inducing mature Wolffian duct cell aggregates from the early Wolffian duct cells obtained in stage 3. The early Wolffian duct cells may be the cells cryopreserved and then thawed by the method of the present application. In step 4, the early Wolffian duct cells are cultured in the presence of a glial cell line-derived neurotrophic factor (GDNF), a fibroblast growth factor, a retinoic acid receptor agonist, a GSK3β inhibitor and a Yes-associated protein (YAP) activity inhibitor under a suspension culture condition.

In step 4, the concentration of a glial cell line-derived neurotrophic factor (GDNF) is generally 1 ng/ml to 10 μg/ml, preferably 10 ng/ml to 1 μg/ml, more preferably 50 ng/ml to 200 ng/ml, and for example about 100 ng/ml.

When FGF1 is used as a fibroblast growth factor, its concentration in the medium is generally 2 ng/ml to 20 μg/ml, preferably 20 ng/ml to 1 μg/ml, more preferably 100 ng/ml to 400 ng/ml, and for example about 200 ng/ml.

When TTNPB is used as a retinoic acid receptor agonist, its concentration in the medium is generally 0.001 μM to 10 μM, preferably 0.01 μM to 1 μM, more preferably 0.05 μM to 0.2 μM, and for example about 0.1 μM.

When CHIR99021 is used as a GSK3β inhibitor, its concentration in the medium is generally 0.03 μM to 300 μM, preferably 0.3 μM to 30 μM, more preferably 1.5 μM to 6 μM, and for example about 3 μM.

A known inhibitor may be appropriately used as a Yes-associated protein (YAP) activity inhibitor. Examples of YAP activity inhibitors include Thiazovivin, which has both YAP inhibitory activity and ROCK inhibitory activity. When Thiazovivin is used, its concentration in the medium is 0.1 μM to 100 μM, preferably 1 μM to 50 μM, more preferably 5 μM to 20 μM, for example about 10 μM.

In stage 4, early Wolffian duct cells are cultured in a non-adhesive culture plate. A plate not artificially treated (for example, not coated with an extracellular matrix) for the purpose of improving the adhesion between the cell culture plate and cells, or a plate artificially treated for suppressing the adhesion (for example, coated with polyhydroxyethyl methacrylic acid (poly-HEMA)) can be used as a non-adhesive cell culture plate.

The culture period of stage 4 may be 24 to 72 hours, for example about 48 hours. In stage 4, mature Wolffian duct cell aggregates are induced. The size of a mature Wolffian duct cell aggregate is usually 100 to 1000 μm, preferably about 300 μm. The generation of mature Wolffian duct cells can be confirmed by the expressions of CK8, PAX2 and E-CADHERIN.

When the culture in stage 4 is performed using the early Wolffian duct cells obtained from pluripotent stem cells through stages 1 to 3, mature Wolffian duct cells can be obtained at a rate of about 50% or more, preferably about 60%, for example about 70% of the total cells obtained. Under a suspension culture condition, mature Wolffian duct cells form aggregates in which mature Wolffian duct cells mainly accumulate, and therefore a mature Wolffian duct cell mass can be physically isolated under a microscope easily, for example by pipetting.

Stage 4'

Stage 4' is the step of inducing mature Wolffian duct cell aggregates from early Wolffian duct cells obtained in stage 3. The early Wolffian duct cells may be those cryopreserved and then thawed by the method of the present application. In stage 4', early Wolffian duct cells are cultured in the presence of a GSK3β inhibitor, a BMP inhibitor, a fibroblast growth factor, a retinoic acid receptor agonist, a glial cell line-derived neurotrophic factor (GDNF) and preferably a ROCK inhibitor under a suspension culture condition. The medium used in step 4' is the same as that used in stage 3, or the medium used in stage 3 further supplemented with a ROCK inhibitor. The ROCK inhibitor is used for suppressing apoptosis.

When Y27632 is used as a ROCK inhibitor, its concentration in the medium is generally 0.1 μM to 100 μM, preferably 1 μM to 50 μM, more preferably 5 μM to 20 μM, and for example about 10 μM.

In stage 4', the early Wolffian duct cells are cultured in a non-adhesive culture plate as in stage 4. The culture period of stage 4' may be 24 hours to 72 hours, for example, about 48 hours. In stage 4', mature Wolffian duct cell aggregates are induced. The generation of mature Wolffian duct cells can be confirmed by the expressions of CK8, PAX2 and E-CADHERIN.

Under a suspension culture condition, obtained mature Wolffian duct cells form aggregates in which mature Wolffian duct cells mainly accumulate, and therefore a mature Wolffian duct cell mass can be easily physically isolated under a microscope, for example by pipetting.

Stage 5

Stage 5 is the step of inducing ureteric bud-like tissues from mature Wolffian duct cell aggregates obtained in stage 4. In stage 5, the mature Wolffian duct cell aggregates are cultured in the presence of a glial cell line-derived neurotrophic factor (GDNF), a fibroblast growth factor, a retinoic acid receptor agonist, a GSK3β inhibitor and a Yes-associated protein (YAP) activity inhibitor under a three-dimensional culture condition. In this step, the mature Wolffian duct cell aggregates obtained in stage 4 are isolated and then embedded and cultured in a three-dimensional scaffold material diluted with the medium under a three-dimensional culture condition. The medium used in step 5 is the same as that used in stage 4.

The three-dimensional scaffold material is not particularly limited. Various three-dimensional scaffold materials for constructing a three-dimensional structure of cultured cells are known and commercially available. For example, a collagen-based material, a polymer-based material such as polycaprolactone and polyglycolic acid, or a complex thereof can be used. The form of the three-dimensional scaffold material is also not particularly limited, and examples thereof include a sponge-like structure. Further, the three-dimensional scaffold material may be a material derived from a living body, such as extracellular matrix and basement membrane. Specifically, the three-dimensional scaffold material can include Matrigel™ (Becton, Dickinson and Company), type I collagen gel and type IV collagen gel.

Matrigel™ basement membrane matrix is a soluble basement membrane preparation extracted from Engelbreth-Holm-Swarm (EHS) mouse sarcoma, which is rich in extracellular matrix proteins, and composed primarily of laminin, collagen IV, entactin and heparan sulfate proteoglycan. In addition, it includes other growth factors such as TGF-β, fibroblast growth factor, tissue plasminogen activator, and EHS. Matrigel™ basement membrane matrix (Matrigel) is preferably used as the three-dimensional scaffold material used in stage 5 of the present application.

When Matrigel is used as a three-dimensional scaffold material, Matrigel is generally diluted at 1:0.5 to 1:2, for example about 1:1 in a medium.

The culture period of stage 5 may be 5 to 30 days, preferably 7 to 20 days, for example, about 15 days. In stage 5, the induction of ureteric bud-like tissues can be confirmed by the expressions of the markers, such as GATA3, RET, PAX and CALB1. The size of the obtained ureteric bud-like tissue is usually 30 to 200 μm, preferably about 50 μm. Ureteric bud-like tissue usually branches 2 to 3 times. The formation of ureteric bud-like tissue having branching structure can be confirmed under a microscope.

Stage 5'

Stage 5' is the step of inducing ureteric bud-like tissues from mature Wolffian duct cell aggregates obtained in stage 4'. In stage 5', the mature Wolffian duct cell aggregates are cultured in the presence of a GSK3β inhibitor, a BMP inhibitor, a fibroblast growth factor, a retinoic acid receptor agonist and a glial cell line-derived neurotrophic factor (GDNF) under a suspension culture condition. In this step, the mature Wolffian duct cell aggregates obtained in stage 4' are isolated and cultured in a medium containing low-concentration of a three-dimensional scaffold material under a suspension culture condition. The medium used in step 5' is the medium used in stage 3 further supplemented with a three-dimensional scaffold material. The three-dimensional scaffold material used in step 5' is the same as that used in stage 5.

When Matrigel is used as a three-dimensional scaffold material, its concentration in the medium is generally 1 to 5%, for example about 2%.

The culture period of stage 5' may be 1 to 15 days, preferably 3 to 10 days, for example about 6 days. In stage 5', the induction of ureteric bud-like tissues can be confirmed by the expressions of the markers, such as GATA3, RET, PAX and CALB1. The formation of ureteric bud-like tissue having branching structure can be confirmed under a microscope.

Stage 6

Stage 6 is the step of inducing ureteric bud-like organoids from ureteric bud-like tissues. The ureteric bud-like tissues are isolated and cultured in the medium containing low-concentration of a three-dimensional scaffold material in the presence of a GSK3β inhibitor, a BMP inhibitor, a fibroblast growth factor, a retinoic acid receptor agonist and a glial cell line-derived neurotrophic factor (GDNF) under a suspension culture condition. The ureteric bud-like tissues may be obtained by the method of the present application or by another known method. The medium and three-dimensional scaffold material used in step 6 are the same as those used in stage 5'.

In the specification and claims of the present application, the expression "ureteric bud-like organoid" means a ureteric bud-like self-organized structure having branching structure obtained by isolating and culturing. The size of a ureteric bud-like organoid is usually about 100 to about 1000 μM. A ureteric bud-like organoid usually branches 3 to 5 times. The induction of a ureteric bud-like tissue can be confirmed by the expressions of the markers, such as GATA3, RET, PAX and CALB1. The branching structure of a ureteric bud-like tissue can be confirmed under a microscope.

When Matrigel is used as a three-dimensional scaffold material, its concentration in the medium is generally 1 to 51, for example about 21.

The culture is performed for 5 to 30 days, preferably 7 to 20 days, for example about 14 days. In stage 6, the formation of a ureteric bud-like organoid can be confirmed under a microscope. The polarity of a ureteric bud-like organoid can be confirmed by the expressions of LAMININ and EZRIN.

Stage 7

Stage 7 is the step of maintaining ureteric bud-like organoids. The ureteric bud-like organoids are maintained by repeating the step of truncating the tip regions of ureteric bud-like organoids to obtain ureteric bud-like tip tissues and the step of culturing the obtained ureteric bud-like tip tissues in the medium containing low-concentration of a three-dimensional scaffold material in the presence of a GSK3β inhibitor, a BMP inhibitor, a fibroblast growth factor, a retinoic acid receptor agonist and a glial cell line-derived neurotrophic factor (GDNF) under a suspension culture condition. The ureteric bud-like organoid may be obtained by the method of the present application or by another known method. The steps of stage 7 can be repeated at least three times. The number of repetitions is not particularly limited and a desired number of times may be repeated. The medium and the three-dimensional scaffold material used in step 7 are the same as those used in stage 5'.

In the specification and claims of the present application, the expression "ureteric bud-like tip tissue" means the tissue obtained by truncating the tip region of the branch of a ureteric bud-like organoid. The size of a ureteric bud-like tip tissue is usually 30 to 200 μm, preferably about 50 μm. A ureteric bud-like tip tissue can be appropriately cultured to form branching structure and then the ureteric bud-like organoid can be generated.

The culture in one step is performed for 1 to 15 days, preferably 3 to 10 days, for example about 7 days. The formation of branching ureteric bud-like tissue can be confirmed under a microscope. The polarity of a ureteric bud-like tissue can be confirmed by the expressions of LAMININ and EZRIN.

Stage 6'

Stage 6 is the step of expansion-culturing ureteric bud-like tip tissues. The tissues in a ureteric bud-like tissue culture are dissociated into single cells and the single cells are cultured in the presence of a glial cell line-derived neurotrophic factor, a fibroblast growth factor, a retinoic acid receptor agonist, a GSK3β inhibitor and a Yes-associated protein (YAP) activity inhibitor under a three-dimensional culture condition. In this step, the ureteric bud-like tissue culture is dissociated into single cells and the cells are seeded and cultured on the hydrogel obtained by diluting a three-dimensional scaffold material with the medium under a three-dimensional culture condition. The ureteric bud-like tissue culture may be obtained by the method of the present application or by another known method. The medium used in step 6' is the same as that used in step 4.

As a means for dissociating cells, a conventionally known means for dissociating cell aggregates may be appropriately used. Examples of the means include a means for mechanically dissociating cells, and a dissociation means using dissociation solution having protease activity and collagenase activity, such as Accutase and Accumax, or having only collagenase activity. The means preferably used in stage 6' is the means for dissociating cell aggregates using dissociation solution having protease activity and collagenase activity (preferably Accutase) and mechanically and finely dispersing them into single cells.

When Matrigel is used as a three-dimensional scaffold material, its concentration in the hydrogel is generally 30 to 70%, for example about 50%.

The culture is performed for 1 to 15 days, preferably 3 to 10 days, for example about 6 days or about 7 days. In stage 6', the induction of ureteric bud-like tip tissues can be confirmed by the expressions of the makers, such as CK8, GATA3 and RET.

Stage 7'

Stage 7' is the step of inducing ureteric bud-like organoids from ureteric bud-like tip tissues obtained in stage 6'. The ureteric bud-like tip tissues obtained in stage 6' are cultured in the medium containing low-concentration of a three-dimensional scaffold material in the presence of a GSK3β inhibitor, a BMP inhibitor, a fibroblast growth factor, a retinoic acid receptor agonist and a glial cell line-derived neurotrophic factor (GDNF) under a suspension culture condition. The medium and three-dimensional scaffold material used in step 7' are the same as those used in stage 5'.

The culture is performed for 5 to 30 days, preferably 7 to 20 days, for example about 14 days. In stage 7', the formation of a ureteric bud-like organoid can be confirmed under a microscope. The polarity of a ureteric bud-like organoid can be confirmed by the expressions of LAMININ and EZRIN.

Stage 7"

Stage 7" is the step of inducing collecting duct progenitor cells from ureteric bud-like tip tissues. The ureteric bud-like tip tissues obtained in stage 6' are isolated and then cultured in the presence of a Wnt signal inhibitor and a TGFβ signal inhibitor under an adherent culture condition.

When IWR-1 is used as a Wnt signal inhibitor, its concentration in the medium is 0.01 μM to 100 μM, preferably 0.1 μM to 10 μM, more preferably 0.5 μM to 2 μM, and for example about 1 μM.

When A83-01 is used as a TGFβ inhibitor, its concentration in the medium is generally 0.01 μM to 100 μM, preferably 0.1 μM to 10 μM, more preferably 0.5 μM to 2 μM, and for example about 1 μM.

In stage 7", ureteric bud-like tissues are cultured in a cell culture plate coated with extracellular matrix proteins, e.g. laminin. The culture is performed for 1 to 15 days, preferably 3 to 10 days, for example about 7 days. The generation of a collecting duct progenitor cell can be confirmed by the expression of aquaporin 2 (AQP2) in the cells.

EXAMPLES

The present invention is described in more detail referring to following Examples. The present invention, however, is not limited by those Examples in any way.

Material and Methods

Cell Culture

The experiments using human induced pluripotent stem cells (hiPSCs) and embryonic stem cells (hESCs) were approved by the Ethics Committee of the Department of Medicine and Graduate School of Medicine, Kyoto University, and informed consent was obtained from donor subjects from whom hiPSCs were derived in accordance with the Institutional Review Board.

hiPSCs/ESCs were maintained with feeder-free cultures using Stem Fit AK02N medium (Takara) on cell culture plates coated with iMatrix-511 silk (Nippi). The cells were passaged using 0.5 mM EDTA/PBS (Thermo Fisher Scientific) every four days and routinely tested for mycoplasma contamination.

Directed Differentiation

Details of the growth factors and the small molecules used in the Examples are shown in Table 1.

TABLE 1

| Name | Company | Catalog Number |
| --- | --- | --- |
| Activin A | R&D | 338-AC |
| A83-01 | WAKO | 035-24113 |
| BMP4 | Peprotech | AF-120-05ET |
| CHIR99021 | Stem RD | CHIR-010 |
| FGF1 | R&D | 231-BC |
| FGF2 | WAKO | 060-04543 |
| FGF8 | Peprotech | 100-25 |
| FGF9 | Peprotech | 100-23 |
| GDNF | R&D | 212-GD |
| LDN193189 | Axon Medchem | Axon1509 |
| PD0325901 | WAKO | 162-25291 |
| retinoic acid | MERCK | R2625-50MG |
| TTNPB | Santa Cruz Biotechnology | sc-203303 |
| Thiazovivin | Santa Cruz Biotechnology | SCB-SC-361380-10 |

Anterior Primitive Streak (APS) Induction

Undifferentiated hiPSCs/ESCs were plated at a density of $2.5 \times 10^4$ cells/cm$^2$ onto tissue culture plates in maintenance medium with 10 µM Y-27632 and iMatrix-511 silk. After 24 h, the cells were washed with PBS and treated with Essential 6 medium (Thermo Fisher Scientific) containing 100 ng/ml Activin A (R&D Systems) and 3 µM CHIR99021 (Stem RD) with or without 10 ng/ml bone morphogenetic protein (BMP)4 (PeproTech) for 24 h.

Mesoderm Induction

Anterior primitive streak cells were treated with Essential 6 medium containing 0.1 µM LDN193189 (Axon Medchem), 1 µM A83-01 (WAKO) and 3 µM CHIR99021 for 24 h to induce presomitic mesoderm cells. For early somite induction, medium was changed to Essential 6 medium with 1 µg/ml retinoic acid (RA; MERCK) and 0.5 µM PD0325901 (WAKO) for 24 h.

To induce anterior intermediate mesoderm, the anterior primitive streak cells were treated with 200 ng/ml fibroblast growth factor (FGF) 8 (Peprotech), 0.1 µM 4-[(E)-2-(5,6,7, 8-Tetrahydro-5,5,8,8-tetramethyl-2-naphthalenyl)-1-propenyl]-benzoic acid (TTNPB; Santa Cruz Biotechnology), 1 µM A83-01 and 0.1 µM LDN193189 for 2 days. Then, the cells were replated onto Matrigel-coated plates at a density of $1 \times 10^5$ cells/cm$^2$ in the anterior intermediate mesoderm induction medium with 10 µM Y-27632 and incubated for an additional 24 h.

Wolffian Duct Induction

Anterior intermediate mesoderm cells were treated with Essential 6 medium containing 1 µM CHIR99021, 0.1 µM LDN193189, 200 ng/ml FGF8 and 100 ng/ml glial cell line-derived neurotrophic factor (GDNF; R&D Systems) with or without 0.1 µM TTNPB for 2 days to enhance Wolffian duct leading edge cell induction. Then, the cells were dissociated into single cells by gentle pipetting after treatment with Accutase (Innovative Cell Technologies). The cells were seeded onto low-attachment 96-well plates (Sumitomo Bakelite) at a density of $1 \times 10^4$ cells/well in Essential 6 medium with 100 ng/ml GDNF, 200 ng/ml FGF1 (R&D Systems), 0.1 µM TTNPB, 3 µM CHIR99021 and 10 µM Thiazovivin (Santa Cruz Biotechnology) and incubated for 2 days to induce mature Wolffian duct aggregates.

Ureteric Bud Branching

The resulting mature Wolffian duct aggregates were embedded into 30 µl Matrigel (BD Biosciences) diluted with Essential 6 medium (1:1) in low-attachment 96-well plates and incubated for 30 min. After the solidification of Matrigel, Essential 6 medium supplemented with 100 ng/ml GDNF, 200 ng/ml FGF1, 0.1 µM TTNPB, 3 µM CHIR99021 and 10 µM Thiazovivin was added.

Improved Method for Inducing Mature Wolffian Duct Aggregates and Ureteric Buds The early Wolffian duct cells induced from anterior intermediate mesoderm cells were treated with Accutase and then dissociated into single cells by gentle pipetting. The cells were plated at a density of $1 \times 10^4$ cells/well in Essential 6 medium containing 1 µM CHIR99021, 0.1 µM LDN193189, 200 ng/ml FGF8, 100 ng/ml GDNF, 0.1 µM TTNPB and 10 µM Y-27632 on a low-attachment 96-well plate to induce mature Wolffian duct aggregates for 2 days.

The mature Wolffian duct aggregates were then cultured in Essential 6 medium containing 1 µM CHIR99021, 0.1 µM LDN193189, 200 ng/ml FGF8, 100 ng/ml GDNF, 0.1 µM TTNPB and 2% Matrigel under a suspension culture condition to induce ureteric bud tissues.

Cryopreservation of Wolffian Duct Cells

The early Wolffian duct cells induced from anterior intermediate mesoderm cells in 24-well plates were washed once with 0.5 ml PBS and then incubated with 0.3 ml Accutase for 3 minutes at 37° C. After pipetting, the cells were collected. After 2.7 ml DMEM and 10% FBS solution were added, the cells were centrifuged at 900 RPM for 5 minutes. The supernatant was removed, and the cells were then suspended in 3 ml stem cell banker and dispensed into three stock tubes at 1 ml. After being slowly frozen at −80° C. for 24 hours, it was transferred to a liquid nitrogen tank and stored.

Progression of Branching of Ureteric Bud Tissues

Ureteric bud tissues were mechanically isolated from mature Wolffian duct aggregates under a microscope and cultured in Essential 6 medium containing 1 µM CHIR99021, 0.1 µM LDN193189, 200 ng/ml FGF8, 100 ng/ml GDNF, 0.1 µM TTNPB and 2% Matrigel under a suspension culture condition.

The tip regions of the generated structures were mechanically truncated and cultured in Essential 6 medium containing 1 µM CHIR99021, 0.1 µM LDN193189, 200 ng/ml FGF8, 100 ng/ml GDNF, 0.1 µM TTNPB and 2% Matrigel under a suspension culture condition.

Expansion Culture of Ureteric Bud Organoids

The ureteric bud tissues were treated with Accutase for 3 minutes at 37° C. and dissociated without mechanically isolated. The cells were suspended in DMEM/F12+B27 (vit A free) medium supplemented with the factors, 3 µM CHIR99021, 10 µM Thiazovivin, 200 ng/ml FGF1, 0.1 µM TTNPB, and 100 ng/ml GDNF. The single cells obtained from 5 to 6 aggregates were plated and cultured on hydrogel prepared on a 48-well plate. The hydrogel was prepared by incubating DMEM/F12+B27 (vit A free) medium containing 50% Matrigel for 30 minutes at 37° C. to coagulate.

The cells were cultured for 6 days, and 1 ml Cell recovery solution was then added to the medium. The cells were incubated for 1 hour at 4° C. The hydrogel was dissolved and the cells were transferred to a tube. Two milliliters of Cell recovery solution was further added to the culture, followed by gentle pipetting. The cells were centrifuged at 500 G for 5 minutes. The supernatant was discarded and the cells were washed with 2 ml Essential 6 medium. The cells were further centrifuged at 500 G for 5 minutes and the supernatant was discarded. The cells were cultured on 35 mm non-adhesive plates in Essential 6 medium supplemented with the factors, 1 µM CHIR99021, 0.1 µM LDN193189, 200 ng/ml FGF8, 100 ng/ml GDNF, 0.1 µM TTNPB and 2% Matrigel. On day 4, each aggregate was transferred to each well of a 96-well plate and further cultured.

Induction of Collecting Duct Progenitor Cells

In the method of expansion-culturing ureteric bud organoids, cells seeded on hydrogel were cultured for 7 days and then dissociated into single cells by treatment with Accutase. The single cells were seeded on iMatrix-silk-coated plates in Essential 6 medium containing 1 µM IWR-1 and 1 µM A83-01 and then cultured for further 7 days.

Immunostaining

The cells were fixed with 4% PFA/PBS for 20 min at 4° C. After washing with PBS, the cells were blocked with 1% normal donkey serum (Millipore) and 3% bovine serum albumin (BSA; Nacalai Tesque)/PBST (PBS/0.25% Triton X-100) for 1 h at room temperature. Primary antibodies were diluted in blocking solution and incubated with samples overnight at 4° C. Secondary antibodies were incubated for 1 h at room temperature.

Cellular aggregates were fixed with 4% PFA/PBS overnight at 4° C. Fixed aggregates were treated with 30% sucrose buffer and then frozen with OCT compound (Tissue-Tek) to make frozen sections by cryosectioning. The frozen sections were washed with distilled water and incubated with blocking solution for 1 h at room temperature. Primary antibodies were diluted in blocking solution and incubated with samples overnight at room temperature. The cells were then incubated with secondary antibodies for 1 h at room temperature. Details of the antibodies used in the examples are shown in Tables 2 and 3.

TABLE 2

| Antigen | Animal | Company | Catalog Number |
| --- | --- | --- | --- |
| BRACHYURY | goat | R&D | AF2085 |
| CALB1 | mouse | Sigma | C9848 |
| CADHERIN 16 | rabbit | Proteintech | 15107-1-AP |
| CK8 | mouse | Abcam | ab9023 |
| CK19 | rabbit | Abcam | ab52625 |
| E-CADHERIN | mouse | BD | 610181 |
| FOXF1 | goat | R&D | AF4798 |
| GATA3 | rabbit | Cell signaling | 5852S |
| GATA3 | goat | R&D | AF2605 |
| GFP | rat | Nacalai Tesque | 04404-26 |
| GFP | rabbit | Thermo Fisher Scientific | A-11122 |
| HOXB4 | rat | DSHB | 112 |
| Ki67 | mouse | BD | 556003 |
| LHX1 | mouse | R&D | MAB2725 |
| mCherry | rabbit | Clontech | 632496 |
| PAX2 | rabbit | Covance | PRB-276P |
| PAX2 | goat | R&D | AF3364 |
| PAX2 | rabbit | Thermo Fisher Scientific | 71-6000 |
| PAX3 | mouse | DSHB | AB528426 |
| RET | goat | R&D | AF1485 |

TABLE 2-continued

| Antigen | Animal | Company | Catalog Number |
| --- | --- | --- | --- |
| SIX2 | rabbit | Proteintech | 11562-1-AP |
| SOX17 | goat | R&D | AF1924 |
| TBX6 | goat | R&D | AF4744 |

TABLE 3

| Antigen | Animal | Company | Catalog Number |
| --- | --- | --- | --- |
| LAMININ | rabbit | Sigma-Aldrich | L9393 |
| EZRIN | mouse | Abcam | Ab4069 |

Flow Cytometry

After dissociation with Accutase, the cells were fixed, permeabilized and blocked with a BD Cytofix/Cytoperm Kit (Becton Dickinson). Then the cells were incubated with primary antibodies diluted at 1:100 in blocking solution for 30 min at room temperature. After washing twice, the cells were incubated with secondary antibodies diluted at 1:500 in blocking solution for 30 min at room temperature. The cells were then analyzed using FACS AriaII cell sorter (Becton Dickinson).

Results

Differentiation of hiPSCs into Anterior Intermediate Mesoderm Cells

We first aimed to establish a presomitic mesoderm induction method from hiPSCs following anterior primitive streak differentiation (FIGS. 1A and 5A), because hPSC-derived anterior primitive streak cells have been reported to differentiate into presomitic mesoderm in vitro (K. M. Loh et al, Cell 166 (2016) 451-467). We previously established an anterior primitive streak induction method using Activin A and a GSK3β inhibitor, CHIR99021, from hPSCs (S. I. Mae et al, Nat. Commun. 4 (2013) 1367). Therefore, we treated an OSR-GFP knockin hiPSC line (3D45) we had previously generated (S. I. Mae et al, Nat. Commun. 4 (2013) 1367) under feeder-free cultures with 100 ng/ml Activin A and 3 µM CHIR99021 to induce BRACHYURY$^+$ cells in serum-free two-dimensional cultures (FIG. 5B). To induce presomitic mesoderm from anterior primitive streak, we modified a previously reported method (K. M. Loh et al, Cell 166 (2016) 451-467) and observed the expression of TBX6, a marker for presomitic mesoderm (FIG. 5C). To assess the developmental potential of hiPSC-derived TBX6$^+$ cells, we used a MEK inhibitor, PD0325901, that inhibits FGF signaling and RA, and found the differentiation of PAX3$^+$ early somite cells (FIG. 5D). These results suggest the establishment of a presomitic mesoderm induction method from hiPSCs through anterior primitive streak differentiation.

Although treatment with FGF9 and RA was reported to induce anterior intermediate mesoderm from early presomitic mesoderm (M. Takasato et al, Nature 526 (2015) 564-568), the expression of Osr1, one of the earliest markers for intermediate mesoderm, is detected earlier than Fgf9 in mouse intermediate mesoderm development (J. S. Colvin et al, Dev. Dyn. 216 (1999) 72-88; P. L. So et al, Mech. Dev. 84 (1999) 157-160; Q. Wang et al, Dev. Biol. 288 (2005) 582-594). We therefore used FGF8, which is expressed in presomitic mesoderm and intermediate mesoderm (B. Wilm et al, Dev. Biol. 271 (2004) 176-189), and a RA agonist, TTNPB, which can induce OSR1 expression (T. Araoka et al, PLoS One 9 (2014), e84881), to determine the developmental origin of anterior intermediate mesoderm. Immunostaining analysis for OSR1 (GFP) and an anterior intermediate mesoderm marker, GATA3, showed that the combination treatment did not induce presomitic mesoderm cells into OSR1⁺GATA3⁺ anterior intermediate mesoderm cells although the cells differentiated into OSR1⁺GATA3⁻ intermediate mesoderm-like cells (FIG. 1B). Unexpectedly, we found that anterior primitive streak cells differentiated into OSR1⁺GATA3⁺ anterior intermediate mesoderm-like cells with the same treatment (FIG. 1B). A previous report indicated that presomitic mesoderm exposed to longer Wnt stimulation than anterior primitive streak can differentiate into nephron progenitor (NP) cells following posterior intermediate mesoderm induction (M. Takasato et al, Nature 526 (2015) 564-568). By modifying previously reported protocols for nephron progenitor induction from presomitic mesoderm (A. Taguchi et al, Cell Stem Cell 14 (2014) 53-67; M. Takasato et al, Nature 526 (2015) 564-568; R. Morizane et al, Nat. Biotechnol. 33 (2015) 1193-1200), we could differentiate presomitic mesoderm into OSR1⁺SIX2⁺ nephron progenitor-like cells (FIG. 5E). These data indicates that the developmental origins of anterior and posterior intermediate mesoderms are different.

Establishment of a Robust Induction Method for Anterior Intermediate Mesoderm Cells In order to improve the induction efficiency of anterior intermediate mesoderm cells, we added a TGFβ signaling inhibitor, A83-01, to FGF8 and TTNPB and found the differentiation of SOX17⁺ definitive endoderm cells was diminished (FIG. 5F). The induced OSR1⁺GATA3⁺ intermediate mesoderm-like cells also expressed other anterior intermediate mesoderm markers including PAX2, LHX1 and HOXB4 (FIG. 1C) and had induction rates of OSR1⁺, GATA3⁺, LHX1⁺ and HOXB4⁺ cells of 46.6±13.6%, 35.8±18.2%, 69.6±16.5% and 67.2±14.5% (n=4), respectively (FIG. 1D), confirming that the three-factor (i.e. FGF8, TTNPB and A83-01) treatment produced anterior intermediate mesoderm cells from anterior primitive streak.

We next examined the effects of BMP signals on each step during anterior primitive streak and anterior intermediate mesoderm induction because BMP signals play crucial roles in various aspects of kidney development (L. Oxburgh et al, Pediatr. Nephrol. 29 (2014) 531-536). Adding BMP4 to the anterior primitive streak induction stage increased the OSR1⁺GATA3⁺ cell induction rate to around 70% of the total cells obtained (FIGS. 1E, F and H). On the other hand, while adding a BMP signal inhibitor, LDN193189, to the anterior intermediate mesoderm induction stage did not change the induction efficiency of OSR1⁺GATA3⁺ cells, the addition of BMP4 inhibited the differentiation, suggesting that the BMP signal is not necessary for anterior intermediate mesoderm differentiation from anterior primitive streak (FIGS. 1E, G and H). These results are consistent with the finding that Smad1, a downstream molecule of the Bmp signaling pathway, is not phosphorylated in the anterior intermediate mesoderm region during early chick development (S. Faure et al, Dev. Biol. 244 (2002) 44-65).

Next, we confirmed that our anterior intermediate mesoderm cell differentiation protocol was applicable to multiple hPSC lines, including an hiPSC line that constitutively expresses mCherry (511-3E; F. Oceguera-Yanez et al, Methods 101 (2016) 43-55), an hiPSC line established from a patient with autosomal dominant polycystic kidney disease (ADPKD) (CiRA00009; T. Ameku et al, Sci. Rep. 6 (2016) 30013) and an human embryonic stem cell (hESC) line (KhES3; H. Suemori et al, Biochem. Biophys. Res. Commun. 345 (2006) 926-932) in addition to 3D45, affirming the robustness of our differentiation method from hPSCs to anterior intermediate mesoderm cells (FIG. 6).

Induction of Wolffian Duct Cells

Because the Wolffian duct is formed dorsally from anterior intermediate mesoderm under the influence of Wnt proteins secreted from surface ectoderm (T. Obara-Ishihara et al, Development 126 (1999) 1103-1108), we hypothesized that exogenous WNTs might be necessary for Wolffian duct differentiation from anterior intermediate mesoderm cells (FIG. 2A). The addition of CHIR99021 to anterior intermediate mesoderm cells enhanced OSR1⁻GATA3⁺PAX2⁻ cell differentiation (FIG. 2B). Considering the decline of Osr1 expression is a significant marker of Wolffian duct induction (F. Costantini et al, Dev. Cell 18 (2010) 698-712), this finding suggested the initiation of Wolffian duct differentiation. On the other hand, the supplementation of a WNT signaling inhibitor, IWR-1, prolonged OSR1 expression and diminished GATA3 and PAX2 expressions (FIG. 2B).

Conflicting results about the effects of Bmp4 secreted from surface ectoderm and lateral plate mesoderm on Wolffian duct induction have been reported (T. Obara-Ishihara et al, Development 126 (1999) 1103-1108; T. Yoshino et al, Nat. Commun. 7 (2016) 12561). We found that, while the addition of BMP4 suppressed Wolffian duct differentiation from anterior intermediate mesoderm cells, LDN193189 treatment enhanced the induction (FIG. 2C), suggesting that both WNT activation and BMP inhibition promote the Wolffian duct induction.

It is known that during elongation, the leading edge cells of the Wolffian duct are attracted by a high dosage of FGF8 and the reduction of FGF signals in the rear cells of Wolffian duct enhances epithelialization (Y. Atsuta et al, Development 142 (2015) 2329-2337). As expected, the supplementation of FGF8 increased the number of GATA3⁺ cells (FIG. 2D). We also found that the addition of GDNF increased the number of GATA3⁺ Wolffian duct cells (FIGS. 2E and F), which expressed a proliferation marker, Ki67, and RET (FIGS. 2F and G). Furthermore, these GATA3⁺ Wolffian duct cells did not express E-CADHERIN but expressed other Wolffian duct markers including PAX2, LHX1 and Cytokeratin 8 (CK8) (FIG. 2H), suggesting the differentiation of leading edge cells of the Wolffian duct. The differentiation protocol in the present application also efficiently generated Wolffian duct cells during elongation from hESC-derived anterior intermediate mesoderm cells (FIG. 7A), and cells that were not differentiated into Wolffian duct cells expressed the neural progenitor marker, PAX6, or OSR1 (FIG. 7B).

It is known that a retinoic acid signal is the upstream of RET, a Wolffian duct cell marker. While early Wolffian duct cells were stably generated by further adding TTNPB to anterior intermediate mesoderm cells (data not shown), the addition of AGN193109, a retinoic acid signaling inhibitor, diminished RET expression (FIGS. 8A and B).

Generation of Branching Ureteric Bud Tissue

It has recently been reported that a combination treatment of 5 factors (Gdnf, Fgf1, RA, CHIR99021 and Y-27632) induces isolated mouse embryonic ureteric bud cells to form branching structures in vitro (S. Yuri et al, Stem Cell Rep. 8 (2017) 401-416). In addition, the suppression of Yes-associated protein (YAP) activity is required for ureteric bud branching (A. Reginensi et al, Nat. Commun. 7 (2016) 12309), and a ROCK inhibitor, Thiazovivin, also inhibits YAP activity (Y. Oku et al, FEBS Open Bio. 5 (2015) 542-549). We replaced RA and Y-27632 in the above combination with TTNPB and Thiazovivin, respectively, and attempted to form Wolffian duct cell aggregates in the presence of the five factors. After 2-day culture under a suspension culture condition, GATA3$^+$ cells were spontaneously separated from other cell types and gathered to form E-CADHENRIN$^+$ epithelial structures (FIGS. 3A and B). Then, we mechanically detached unwanted cells by pipetting (FIG. 3C). The isolated epithelial structures also expressed the mature Wolffian duct markers, RET, CALB1, CDH16 and SOX9 (FIG. 3D).

Next, to induce ureteric bud structures, we embedded the Wolffian duct epithelial aggregates into Matrigel in the presence of the five factors, which resulted in the formation of ureteric bud-like budding structures (FIGS. 3E and F) that expressed GATA3, PAX2, RET and CALB1 (FIG. 3G). Additional culturing induced the expansion of these ureteric bud-like structures and the formation of branching tissues (FIG. 3H). The tip cells expressed RET, while trunk cells were positive for CK19 staining (FIG. 3H), demonstrating the development of polarized branching ureteric bud-like tissues.

Improved Method for Generating Ureteric Bud Tissues

The number of E-CADHERIN-positive cells was increased by extending the culture period for inducing Wolffian duct cells from anterior intermediate mesoderm cells (FIGS. 9A and B), and therefore Wolffian duct epithelial aggregates were expected to be generated using the factors for inducing Wolffian duct cells from anterior intermediate mesoderm cells, i.e. CHIR99021, LDN193189, FGF8, TTNPB and GDNF. After 2-day culture in the presence of these factors and Y-27632 under a suspension culture condition, GATA3$^+$ cells were spontaneously separated from other cell types and gathered to form E-CADHENRIN$^+$ epithelial structures, as in the culture with the above five factors (Gdnf, Fgf1, TTNPB, CHIR99021 and Thiazovivin) (FIG. 9C, left). Unwanted cells could be mechanically detached by pipetting (FIG. 9C, right).

Next, the Wolffian duct aggregates were cultured in Essential 6 medium containing the factors (CHIR99021, LDN193189, FGF8, TTNPB and GDNF) and 2% Matrigel under a suspension culture condition to induce ureteric bud structures (FIGS. 10A and B), resulting in the generation of polarized ureteric buds in which EZRIN on the lumen sides and LAMININ from Matrigel on the basement membrane side were stained (FIGS. 10C and 10D).

Cryopreservation of Wolffian Duct Cells

The early Wolffian duct cells were induced from anterior intermediate mesoderm cells by the above method, and then cryopreserved using stem cell banker (FIG. 11A). By thawing and culturing the cells in the presence of the same factors as in the above improved method, i.e. CHIR99021, LDN193189, FGF8, TTNPB, GDNF and Y-27632, under a suspension culture condition, GATA3$^+$ cells were spontaneously separated from other cell types and gathered to form E-CADHENRIN$^+$ epithelial structures. Unwanted cells could be mechanically detached by pipetting (FIG. 11B).

Progression of Branching of Ureteric Bud Tissues

The polarized ureteric bud tissues obtained by the improved method for generating ureteric bud tissues were mechanically isolated from mature Wolffian duct aggregates under a microscope, and cultured in a medium containing low-concentration Matrigel under a suspension culture condition, resulting in the generation of ureteric bud organoids (FIGS. 12A to 12C). The ureteric bud organoids maintained the polarity (FIG. 12F) and had RET-positive tip cells and CK8-positive trunk cells (FIGS. 12D and 12E).

Next, the tip regions of the branches of the ureteric bud organoids were mechanically truncated and the isolated ureteric bud tip tissues were cultured in a medium containing low-concentration Matrigel under a suspension culture condition. As a result, ureteric bud organoids forming branching structures were generated again (FIGS. 13A to 13C), showing that ureteric bud tip tissues can be maintained by repeating the truncation of the tip regions of generated ureteric bud organoids and the culture of the truncated ureteric bud tip tissues under a suspension culture condition to generate ureteric bud organoids.

Expansion Culture of Ureteric Bud Organoids

The polarized ureteric bud-like tissues obtained by the improved method for generating ureteric bud tissues were dissociated with mature Wolffian duct cell aggregates into single cells by treatment with Accutase. These cells were cultured on hydrogel under a three-dimensional culture condition to generate a number of GATA3/RET co-positive ureteric bud tip tissues (FIGS. 14A to 14D). The generated ureteric bud tip tissues were cultured in a medium containing low-concentration Matrigel under a suspension culture condition to generate ureteric bud organoids (FIGS. 15A to 15D). These results showed that a number of ureteric bud organoids can be generated from one aggregate by dissociating a polarized ureteric bud with a mature Wolffian duct cell aggregate into single cells and culturing the single cells.

Induction of Collecting Duct Progenitor Cells

In the method of expansion-culturing ureteric bud organoids, GATA3/RET co-positive ureteric bud tip tissues obtained by three-dimensional culturing on hydrogel were dissociated into single cells by treatment with Accutase. After culturing under an adherent culture condition, the cells expressed aquaporin 2 (AQP2), a collecting duct progenitor cell marker (FIGS. 16A and B).

What is claimed is:

1. A method for inducing an early Wolffian duct cell comprising the following steps:
   (0) culturing a pluripotent stem cell in the presence of an activator of activin receptor kinase 4,7, a glycogen synthase kinase 3 beta (GSK3β) inhibitor and a bone morphogenetic protein-4 (BMP4) under a two-dimensional culture condition to obtain an anterior primitive streak cell,
   (1) culturing the anterior primitive streak cell in the presence of a fibroblast growth factor 8 (FGF8), a retinoic acid receptor agonist, a transforming growth factor beta (TGFβ) inhibitor, and a BMP inhibitor under a two-dimensional culture condition to obtain an anterior intermediate mesoderm cell culture, and
   (2) culturing the anterior intermediate mesoderm cell culture in the presence of a GSK3β inhibitor, a BMP inhibitor, a FGF and a glial cell line-derived neurotrophic factor under a two-dimensional culture condition.

2. The method according to claim 1, wherein in step (1) the retinoic acid receptor agonist is TTNPB, the TGFβ inhibitor is A83-01, and the BMP inhibitor is LDN193189.

3. The method according to claim 1, wherein in step (2) the GSK3β inhibitor is CHIR99021 and the BMP inhibitor is LDN193189.

4. The method according to claim 1, wherein a retinoic acid receptor agonist is further present in step (2).

5. The method according to claim 4, wherein in step (2) the retinoic acid receptor agonist is TTNPB.

6. The method according to claim 1, wherein in step (0) the activator of activin receptor kinase 4,7 is Activin A and the GSK3β inhibitor is CHIR99021.

7. A method for producing a frozen early Wolffian duct cell comprising the steps of inducing the early Wolffian duct cell by the method according to claim 1 and further cryo-preserving the early Wolffian duct cell.

8. A method for inducing an ureteric bud-like tissue comprising the following steps:

inducing the early Wolffian duct cell by the method according to claim 1;

(3) culturing the early Wolffian duct cell in the presence of a glial cell line-derived neurotrophic factor, a FGF, a retinoic acid receptor agonist, a GSK3β inhibitor and a Yes-associated protein (YAP) activity inhibitor under a suspension culture condition to obtain a mature Wolffian duct cell aggregate; and (4) culturing the mature Wolffian duct cell aggregate in the presence of a glial cell line-derived neurotrophic factor, a FGF, a retinoic acid receptor agonist, a GSK3β inhibitor and a YAP activity inhibitor under a three-dimensional culture condition optionally wherein in steps (3) and (4), the FGF is FGF1, the retinoic acid receptor agonist is TTNPB, the GSK3β inhibitor is CHIR99021, and the YAP activity inhibitor is Thiazovivin.

9. A method for inducing an ureteric bud-like tissue comprising the following steps:

inducing the early Wolffian duct cell by the method according to claim 1;

(3') culturing the early Wolffian duct cell in the presence of a GSK3β inhibitor, a BMP inhibitor, a FGF, a retinoic acid receptor agonist, and a glial cell line-derived neurotrophic factor under a suspension culture condition to obtain a mature Wolffian duct cell aggregate; and (4') culturing the mature Wolffian duct cell aggregate in the presence of a GSK3β inhibitor, a BMP inhibitor, a FGF, a retinoic acid receptor agonist, and a glial cell line-derived neurotrophic factor under a suspension culture condition.

10. The method according to claim 9, wherein in steps (3') and (4') the GSK3β inhibitor is CHIR99021, the BMP inhibitor is LDN193189, the FGF is FGF8, and the retinoic acid receptor agonist is TTNPB.

11. A method for inducing an ureteric bud-like organoid comprising the following steps:

inducing the ureteric bud-like tissue by the method according to claim 8;

(5-1) isolating the ureteric bud-like tissue; and (5-2) culturing the isolated ureteric bud-like tissue in the presence of a GSK3β inhibitor, a BMP inhibitor, a FGF, a retinoic acid receptor agonist, and a glial cell line-derived neurotrophic factor under a suspension culture condition optionally wherein in step (5-2) the GSK3β inhibitor is CHIR99021, the BMP inhibitor is LDN193189, the FGF is FGF8, and the retinoic acid receptor agonist is TTNPB.

12. A method for maintaining an ureteric bud-like organoid, comprising the following steps:

obtaining the ureteric bud-like organoid culture by the method according to claim 11;

(6-1) truncating the tip region of the ureteric bud-like organoid to obtain an ureteric bud-like tip tissue;

(6-2) culturing the ureteric bud-like tip tissue in the presence of a GSK3β inhibitor, a BMP inhibitor, a FGF, a retinoic acid receptor agonist and a glial cell line-derived neurotrophic factor under a suspension culture condition to induce the ureteric bud-like organoid, and (6-3) repeating steps (6-1) and (6-2);

optionally wherein in step (6-2) the GSK3β inhibitor is CHIR99021, the BMP inhibitor is LDN193189, the FGF is FGF8, and the retinoic acid receptor agonist is TTNPB.

13. A method for expansion-culturing ureteric bud-like tip tissue comprising the following steps:

inducing the ureteric bud-like tissue by the method according to claim 8;

(5'-1) dissociating tissue in the ureteric bud-like tissue culture into single cells; and (5'-2) culturing the single cells in the presence of a glial cell line-derived neurotrophic factor, a FGF, a retinoic acid receptor agonist, a GSK3β inhibitor and a YAP activity inhibitor under a three-dimensional culture condition, optionally wherein step (5'-2) the FGF is FGF1, the retinoic acid receptor agonist is TTNPB, the GSK3β inhibitor is CHIR99021, and the YAP activity inhibitor is Thiazovivin.

14. A method for inducing a ureteric bud-like organoid comprising the following steps:

expansion-culturing ureteric bud-like tip tissue by the method according to claim 13; and (6') culturing the ureteric bud-like tip tissue in the presence of a GSK3β inhibitor, a BMP inhibitor, a FGF, a retinoic acid receptor agonist, and a glial cell line-derived neurotrophic factor under a suspension culture condition, optionally wherein in step (6'), the GSK3β inhibitor is CHIR99021, the BMP inhibitor is LDN193189, the FGF is FGF8, and the retinoic acid receptor agonist is TTNPB.

15. A method for inducing a collecting duct progenitor cell comprising the following steps:

culturing ureteric bud-like tip tissue by the method according to claim 13;

(6"-1) dissociating the ureteric bud-like tip tissue into single cells; and (6"-2) culturing the single cells in the presence of a Wnt signal inhibitor and a TGFβ signal inhibitor under an adherent culture condition optionally wherein in step (6"-2) the Wnt signal inhibitor is IWR-1 and the TGFβ signal inhibitor is A83-01.

16. A method for inducing a ureteric bud-like organoid comprising the following steps:

inducing the ureteric bud-like tissue by the method according to claim 9;

(5-1) isolating ureteric bud-like tissue; and (5-2) culturing the isolated ureteric bud-like tissue in the presence of a GSK3β inhibitor, a BMP inhibitor, a FGF, a retinoic acid receptor agonist, and a glial cell line-derived neurotrophic factor under a suspension culture condition optionally wherein in step (5-2) the GSK3β inhibitor is CHIR99021, the BMP inhibitor is LDN193189, the FGF is FGF8, and the retinoic acid receptor agonist is TTNPB.

17. A method for maintaining a ureteric bud-like organoid comprising the following steps:

inducing the ureteric bud-like organoid by the method according to claim 16;

(6-1) truncating the tip region of the ureteric bud-like organoid to obtain ureteric bud-like tip tissue;

(6-2) culturing the ureteric bud-like tip tissue in the presence of a GSK3β inhibitor, a BMP inhibitor, a FGF, a retinoic acid receptor agonist and a glial cell line-derived neurotrophic factor under a suspension culture condition to induce a ureteric bud-like organoid; and (6-3) repeating steps (6-1) and (6-2);

optionally wherein in step (6-2) the GSK3β inhibitor is CHIR99021, the BMP inhibitor is LDN193189, the FGF is FGF8, and the retinoic acid receptor agonist is TTNPB.

18. A method for expansion-culturing ureteric bud-like tip tissue comprising the following steps:

obtaining a ureteric bud-like tissue culture by the method according to claim 9;

(5'-1) dissociating tissue in the ureteric bud-like tissue culture into single cells; and (5'-2) culturing the single cells in the presence of a glial cell line-derived neurotrophic factor, a FGF, a retinoic acid receptor agonist, a GSK3β inhibitor and a YAP activity inhibitor under a three-dimensional culture condition;

optionally wherein in step (5'-2) the FGF is FGF1, the retinoic acid receptor agonist is TTNPB, the GSK3β inhibitor is CHIR99021, and the YAP activity inhibitor is Thiazovivin.

19. A method for inducing a ureteric bud-like organoid comprising the following steps:

obtaining ureteric bud-like tip tissue by the method according to claim 18; and (6') culturing the ureteric bud-like tip tissue in the presence of a GSK3β inhibitor, a BMP inhibitor, a FGF, a retinoic acid receptor agonist, and a glial cell line-derived neurotrophic factor under a suspension culture condition;

optionally wherein in step (6') the GSK3β inhibitor is CHIR99021, the BMP inhibitor is LDN193189, the FGF is FGF8, and the retinoic acid receptor agonist is TTNPB.

20. A method for inducing a collecting duct progenitor cell comprising the following steps:

obtaining ureteric bud-like tip tissue by the method according to claim 18;

(6"-1) dissociating the ureteric bud-like tip tissue into single cells; and (6"-2) culturing the single cells in the presence of a Wnt signal inhibitor and a TGFβ signal inhibitor under an adherent culture condition, optionally wherein in step (6"-2) the Wnt signal inhibitor is IWR-1 and the TGFβ signal inhibitor is A83-01.

\* \* \* \* \*